(12) United States Patent
Adachi et al.

(10) Patent No.: US 10,413,453 B2
(45) Date of Patent: Sep. 17, 2019

(54) STRETCHABLE STRUCTURE FOR ABSORBENT ARTICLE, ABSORBENT ARTICLE COMPRISING SAID STRETCHABLE STRUCTURE, AND METHOD FOR FORMING STRETCHABLE STRUCTURE FOR ABSORBENT ARTICLE

(71) Applicant: DAIO PAPER CORPORATION, Ehime (JP)

(72) Inventors: Takahiko Adachi, Ehime (JP); Akiko Honda, Ehime (JP); Michiyo Taneda, Ehime (JP); Yosuke Mori, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 645 days.

(21) Appl. No.: 15/023,517

(22) PCT Filed: Sep. 25, 2014

(86) PCT No.: PCT/JP2014/075442
§ 371 (c)(1),
(2) Date: Mar. 21, 2016

(87) PCT Pub. No.: WO2015/046338
PCT Pub. Date: Apr. 2, 2015

(65) Prior Publication Data
US 2016/0206481 A1    Jul. 21, 2016

(30) Foreign Application Priority Data

Sep. 30, 2013 (JP) .............................. 2013-203376
Dec. 26, 2013 (JP) .............................. 2013-268794
(Continued)

(51) Int. Cl.
*A61F 13/15* (2006.01)
*A61F 13/49* (2006.01)

(52) U.S. Cl.
CPC .... *A61F 13/4902* (2013.01); *A61F 13/15593* (2013.01); *A61F 13/49011* (2013.01)

(58) Field of Classification Search
CPC ............ A61F 13/4902; A61F 13/15593; A61F 13/49011
(Continued)

(56) References Cited

U.S. PATENT DOCUMENTS 5,876,392 A    3/1999  Hisada
6,293,934 B1*  9/2001  Kumasaka .......... A61F 13/4942
                                                 604/385.27
2004/0102756 A1  5/2004  Ichiura et al.

FOREIGN PATENT DOCUMENTS

EP    0904759 (A2)     3/1999
JP    9-206330 A       8/1997
(Continued)

*Primary Examiner* — Jacqueline F Stephens
(74) *Attorney, Agent, or Firm* — Muncy, Geissler, Olds & Lowe, P.C.

(57) ABSTRACT

A stretchable structure for absorbent article includes: a sheet-like member (12S) that is composed of one air permeable material (120) and has a plurality of pleats (80) arranged at intervals so as not to overlap in a fallen state and inter-pleat portions (85) overlapping in the state in which the pleats (80) are fallen; and elongated resilient and elastic members (90) provided between opposing surfaces (80a and 80b) of the pleats (80) along a longitudinal direction of the pleats (80). The pleats (80) are continuously or intermittently joined in the longitudinal direction of the pleats (80) such that at least the opposing surfaces (80a and 80b) of base portions (81) are not spaced from each other. Outer surfaces of the pleats (80) are not joined to the inter-pleat portions (85) except for both longitudinal ends of the pleats (80). The resilient and elastic members (90) are arranged in the pleats (80) at the tip-side with regard to the base portions (81) and at least both ends of the resilient and elastic members (90) are fixed between the opposing surfaces (80a and 80b) of the pleats (80). The pleats (80) and the inter-pleat portions (85) are contracted by contraction of the resilient and elastic members (90).

9 Claims, 26 Drawing Sheets

(30) Foreign Application Priority Data

Sep. 24, 2014 (JP) ................................ 2014-194021
Sep. 24, 2014 (JP) ................................ 2014-194022

(58) Field of Classification Search
USPC ............ 604/385.24, 385.25, 385.28, 385.29, 604/385.3
See application file for complete search history.

(56) References Cited

FOREIGN PATENT DOCUMENTS

| | | |
|---|---|---|
| JP | 9-262250 A | 10/1997 |
| JP | 09262250 | 10/1997 |
| JP | 11-299829 A | 11/1999 |
| JP | 2004-024304 A | 1/2004 |
| JP | 2004-216124 A | 8/2004 |
| JP | 2004-216124 A | 8/2004 |
| JP | 2009-148447 A | 7/2009 |
| JP | 2009-297096 A | 12/2009 |
| JP | 2011-030791 A | 2/2011 |
| JP | 2011-206218 A | 10/2011 |
| JP | 2013-128515 A | 7/2013 |
| JP | 2013-128515 A | 7/2013 |
| WO | WO00/37006 | 6/2000 |
| WO | WO2007/149674 (A2) | 12/2007 |
| WO | WO2009084643 (A1) | 7/2009 |
| WO | WO2013080782 (A1) | 6/2013 |

\* cited by examiner

STRETCHABLE STRUCTURE FOR ABSORBENT ARTICLE, ABSORBENT ARTICLE COMPRISING SAID STRETCHABLE STRUCTURE, AND METHOD FOR FORMING STRETCHABLE STRUCTURE FOR ABSORBENT ARTICLE

TECHNICAL FIELD

The present invention relates to a stretchable structure for absorbent article formed by attaching elongated resilient and elastic members in an extended state to a sheet, an absorbent article including the stretchable structure, and a method for forming the stretchable structure for absorbent article.

BACKGROUND ART

For example, an underpants-type disposable diaper includes an outer body having a front body part and a back body part, and an inner body that includes an absorber and is fixed to the inner surface of the outer body. The front body part and the back body part of the outer body are joined at the both sides to form a waist opening and a pair of right and left leg openings.

In the underpants-type disposable diaper, elongated resilient and elastic members such as rubber threads are fixed in an extended state at several sections of the outer body along a circumferential direction to form a stretchable structure around the waist portion to enhance the fit to the human body. In particular, diapers including waist-edge resilient and elastic members at the edge portion of the waist opening along the width direction and waist-lower portion resilient and elastic members closer to the crotch portion than the waist-edge resilient and elastic members along the width direction, are widely used due to their relatively good fit to the human body.

Meanwhile, a tape-type disposable diaper has a crotch portion, a ventral-side portion extended to the front side of the crotch portion, a back-side portion extended to the back side of the crotch portion, an absorber provided in an area including the crotch portion, fastening tapes protruding from the both sides of the back portion, and target tapes positioned on the outer surface of the ventral-side portion, to which the fastening tapes are to be fastened. To put the diaper on the wearer's body, the fastening tapes are turned from the both sides of the waist toward the outer surface of the ventral-side portion and are fastened to the target tapes. The tape-type disposable diapers are widely used for infants and for recipients of care (adults) as well. In general, the tape-type disposable diapers are inferior in a fit around the waist to the underpants-type disposable diapers. To improve this, elongated resilient and elastic members such as rubber threads are fixed in the extended state to the back side portion and the fastening tapes along the width direction to form a stretchable structure around the waist portion.

In addition, as an improvement of these stretchable structures, there have been proposed stretchable structures in which two sheet materials are intermittently joined in a stretching direction and a longitudinal direction orthogonal to the stretching direction to form a large number of sheet joined sections, and a plurality of stretchable elongated resilient and elastic members is arranged independent from the two sheet materials so as not to pass through the sheet joined sections (so as to pass through the non-joined sections) between the sheet materials (refer to Patent Documents 1 and 2. These stretchable structures will be hereinafter also referred to as vertical intermittent joined form).

According to the related art, the vertically aligned the sheet joined sections form vertically continuous grooves, and the sections between the grooves form large pleats that swell to the same degree on the both front and back sides. The grooves improve air permeability and the pleats produce excellent fluffy.

For improvement in appearance, there has also been proposed a stretchable structure in which the fixed portion of resilient and elastic members is frilled on the outside (refer to Patent Document 4).

CITATION LIST

Patent Documents

Patent Document 1: JP 2009-297096 A
Patent Document 2: JP 2009-148447 A
Patent Document 3: JP 2004-024304 A
Patent Document 4: JP 2011-030791 A

SUMMARY OF INVENTION

Technical Problem

However, in the conventional stretchable structure, the resilient and elastic members are sandwiched between two air permeable materials to envelop the resilient and elastic members, and there is a limit on reduction in material cost.

A major object of the present invention is to provide a stretchable structure allowing significant reduction in material cost.

Solution to Problem

The present invention as a solution to the foregoing problem is as follows:
<The Invention of Claim 1>
A stretchable structure for absorbent article, comprising: a sheet-like member that is composed of one air permeable material and has a plurality of pleats arranged at intervals so as not to overlap in a fallen state and inter-pleat portions overlapping in the state in which the pleats are fallen; and elongated resilient and elastic members provided between opposing surfaces of the pleats along a longitudinal direction of the pleats, wherein the opposing surfaces of the pleats are continuously or intermittently joined in the longitudinal direction of the pleats such that the opposing surfaces of each pleat are not separated at least at a base portion of the pleat, outer surfaces of the pleat are not joined to the inter-pleat portions except for at both longitudinal ends of the pleats, resilient and elastic members are arranged in the pleats at a tip-side with regard to the base portion and at least both ends of the resilient and elastic members are fixed between the opposing surfaces of the pleats, and the pleats and the inter-pleat portions are contracted by contraction of the resilient and elastic members.
(Operation and Effect)
In the stretchable structure of the present invention, the one air permeable material has the pleats and the resilient and elastic members provided in the pleats, which allows significant reduction in material cost as compared to the conventional stretchable structure in which the resilient and elastic members are sandwiched between two air permeable materials. In addition, although the number of the overlapping materials is three or more at sections where the fallen pleats overlap the inter-pleat portions, the pleats and the inter-pleat portions are not joined but air permeable gaps are formed between the pleats and the inter-pleat portions by their contraction wrinkles to suppress reduction in flexibility and air permeability.

<The Invention of Claim 2>

The stretchable structure for absorbent article according to claim 1, wherein the resilient and elastic members are not continuously fixed in the longitudinal direction between the opposing surfaces of the pleats, and the opposing surfaces of the pleats, except for at least at fixed portions of the resilient and elastic members, are not joined at the tip-side with regard to the base portions.

(Operation and Effect)

Such a structure makes the pleats less prone to reduce in flexibility.

<The Invention of Claim 3>

The stretchable structure for absorbent article according to claim 1 or 2, wherein the pleat protrude to a side opposite to a skin-contact-side, and inter-pleat portions overlap the skin-side of the pleats in the fallen state.

(Operation and Effect)

In most of conventional stretchable structures, only one sheet is positioned at the skin-side of the resilient and elastic members. In this mode, tightening marks are likely to occur on the skin by the resilient and elastic members, which may result in a skin rash. To solve this problem, the layer of the resilient and elastic members positioned at the skin-side may be thickened by increasing the number of sheets positioned at the skin-side of the resilient and elastic members. However, it is not possible to avoid reduction in air permeability simply by increasing the thickness, and the attachment portions of the resilient and elastic members still contact the skin directly. Accordingly, increasing the thickness has no high effect of preventing occurrence of tightening marks.

In contrast to this, according to the stretchable structure described in claim 3, the pleats are tightened and fallen by the contraction of the resilient and elastic members and the wall portions of the fallen pleats at the skin-side and the inter-pleat portions are positioned at the skin-side of the resilient and elastic members, and the wall portions of the pleats at the skin-side and the inter-pleat portions increase in thickness by their contraction wrinkles. That is, the pleats have highly cushioned thick portions formed at the skin-side of the resilient and elastic members. In addition, the wall portions of the pleats at the skin-side increase in thickness by their contraction wrinkles at the base portion-side and tip portion-side of the resilient and elastic members, and therefore, the tightening force of the resilient and elastic members is distributed in the base portion side and the tip portion-side of the pleats. Accordingly, even when the resilient and elastic members are positioned nearer the skin-side than the base portion-side and the tip-side, it is possible to suppress concentration of the tightening force. As a result, tightening marks by the resilient and elastic members are unlikely to be left on the skin. In addition, at the thick portions of the pleats, no sheet-like members attach closely to each other but a large number of air permeable gaps are generated by the contraction wrinkles, thereby suppressing reduction in air permeability. Accordingly, this stretchable structure can allow compatibility between prevention of reduction in air permeability and prevention of occurrence of tightening marks by the elongated resilient and elastic members.

<The Invention of Claim 4>

The stretchable structure for absorbent article according to claim 3, wherein the large number of pleats are provided along the width direction in at least one of front and back areas of the absorbent article, and are fallen in the same direction in at least each area having the pleats.

(Operation and Effect)

When the large number of pleats is arranged, the falling of the pleat in the same direction allows a uniform appearance and easy manufacture.

<The Invention of Claim 5>

The stretchable structure for absorbent article according to claim 3 or 4, wherein protrusion height of pleats is ⅒ to ½ of the interval between the pleats.

(Operation and Effect)

By setting the protrusion height of the pleats to be similar to the interval between the pleats, the three overlapping sheets of the air permeable material becomes large. Accordingly, it is desired to set the protrusion height within the foregoing range.

<The Invention of Claim 6>

The stretchable structure for absorbent article according to claim 3 or 4, wherein resilient and elastic members are arranged to pass between the base portions and tip portions of pleats and pass through a position spaced apart from the base portions and apart from the tip portions, and the opposing surfaces of the pleats, except for at least at the fixed portions of the resilient and elastic members, are not joined at the tip-side with regard to the base portion.

(Operation and Effect)

According to this structure, the larger contraction wrinkles of the pleats are formed to further increase the effect of the present invention described above.

<The Invention of Claim 7>

The stretchable structure for absorbent article according to claims 3, 4, and 6, wherein the protrusion height of the pleats is larger than the interval between the pleats.

(Operation and Effect)

In the case of providing a large number of pleats, increasing the protrusion height of the pleats to be larger than the interval between the pleats, the adjacent pleats overlap each other to make cover portions further thicker. This further increases the effect of the present invention described above.

<The Invention of Claim 8>

The stretchable structure for absorbent article according to any one of claims 1 to 7, wherein the opposing surfaces of the pleats are joined by joined sections that are intermittently arranged in the stretching direction and continuous in the direction crossing the stretching direction, and, at the joined sections, the pleats are fixed in the fallen state and the resilient and elastic members are fixed between the opposing surfaces of the pleats.

(Operation and Effect)

By employing this joint form, the contraction wrinkles extending along the stretching direction are intermittently formed in the stretching direction with excellent air permeability and appearance.

<The Invention of Claim 9>

An absorbent article comprising the stretchable structure for absorbent article according to any one of claims 1 to 8.

(Operation and Effect)

The same advantageous effects as those described in the foregoing claims are produced.

<The Invention of Claim 10>

The absorbent article according to claim 9, wherein the absorbent article is an underpants-type disposable diaper, including: an outer body constituting individually or integrally a front body part and a back body part; and an inner body including an absorber and fixed to an inner surface of the outer body, the front body part of the outer body and the back body part of the outer body being joined at both sides to form side seal portions, thereby forming an annular waist portion and a waist opening and a pair of right and left leg openings, wherein the stretchable structure is provided in an area of the outer body including at least both sides sandwiching the inner body in the width direction such that the longitudinal direction of the pleats is aligned with the width direction.

(Operation and Effect)

The stretchable structure of the present invention is suitable for the area of the outer body of the underpants-type disposable diaper positioned at least at the both sides of the inner body in the width direction.

<The Invention of Claim 11>

The absorbent article according to claim 10, wherein the outer body is composed of a front outer body constituting the front body part and a back outer body constituting the back body part, the front outer body and the back outer body being not continuous but spaced from each other at a crotch-side, and at least one of the front outer body and the back outer body has the pleats formed from one side seal portion to the other side seal portion such that the longitudinal direction of the pleats is aligned with the width direction, and the stretchable structure is formed by the pleats in an area including at least the both sides sandwiching the inner body in the width direction, the protrusion height of the pleats becomes progressively smaller from the side seal portions at the both sides toward the center in the width direction, and edges at the crotch-side swell toward the crotch-side.

(Operation and Effect)

The stretchable structure of the present invention is suitable for the outer body for underpants-type disposable diaper. Underpants-type disposable diapers are divided into an outer integral type in which the outer body is formed integrally at the front and back sides and an outer separated type in which an outer body is split into front and back sides and spaced from each other at the crotch-side. The outer halved type has the advantage that no leg openings for passage of the user's legs need to be punched or only small-area leg openings need to be punched. That is, when cut pieces (hereinafter, also referred to as trims) are discarded, the material loss resulting from the trims (hereinafter, also referred to as trim loss) can be suppressed. However, any attempts to completely eliminate the trim loss would disable the formation of the edges of the leg openings along the peripheries of the groin region and the buttocks. Accordingly, taking the fit around the legs into consideration, it is necessary to partially cut the edges at the crotch-side even in the outer halved type, thereby disabling the complete elimination of the trim loss. In contrast, by employing the stretchable structure of the present invention to progressively decrease the protrusion height of the pleats from the side seal portions on the both sides toward the center in the width direction as described above, the front-back length necessary for the formation of the pleats becomes smaller at the center in the width direction. In addition, by extending the excessive portion to the crotch-side, the pleats of the outer body at the crotch-side can be swollen toward the crotch-side. As a result, it is possible to form the edges of the outer body around the legs at the crotch-side extending to the both sides of the inner body in the width direction along the peripheries of the groin region and the buttocks.

<The Invention of Claim 12>

The absorbent article according to claim 10 or 11, wherein the outer body is composed of a front outer body constituting the front body part and a back outer body constituting the back body part, the front outer body and the back outer body being not continuous but spaced from each other at a crotch-side, and at least one of the front outer body and the back outer body has the pleats formed from one side seal portion to the other side seal portion such that the longitudinal direction of the pleats is aligned with the width direction, and has slits between the pleats in a central portion in the width direction along the longitudinal direction of the pleats, the slits being increased in width at the crotch-side to swell the edges of the crotch-side toward the crotch-side.

(Operation and Effect)

The stretchable structure of the present invention is suitable for the outer body for underpants-type disposable diaper. Underpants-type disposable diapers are divided into an outer integral type in which the outer body is formed integrally at the front and back sides and an outer halved type in which an outer body is split into front and back sides and spaced from each other at the crotch-side. The outer halved type has the advantage that no leg openings for passage of the user's legs need to be punched or only small-area leg openings need to be punched. That is, when cut pieces (hereinafter, also referred to as trims) are discarded, the material loss resulting from the trims (hereinafter, also referred to as trim loss) can be suppressed. However, any attempts to completely eliminate the trim loss would disable the formation of the edges of the leg openings along the peripheries of the groin region and the buttocks. Accordingly, taking the fit around the legs into consideration, it is necessary to partially cut the edges at the crotch-side even in the outer halved type, thereby disabling the complete elimination of the trim loss. In contrast, by forming the slits between the pleats at the central portion in the width direction along the longitudinal side of the pleats and increasing the width of the slits to the crotch-side, the edges at the crotch-side can be swollen toward the crotch-side. As a result, it is possible to form the edges of the outer body around the legs at the crotch-side extending to the both sides of the inner body in the width direction along the peripheries of the groin region and the buttocks.

<The Invention of Claim 13>

The absorbent article according to any one of claims 10 to 12, wherein the pleats are formed at both the front body part of the outer body and the back body part of the outer body from the one side seal portion to the other side seal portion such that the longitudinal direction of the pleats align with the width direction, and the pleats in the front body part and the pleats in the back body part are shifted in position in the front-back direction such that the pleats in the front body part and the pleats in the back body part do not overlap at the side seal portions.

(Operation and Effect)

By employing the structure in which the pleats in the front body part and the pleats in the back body part do not overlap at the side seal portions, the separation strength at the side seal portions less changes in the vertical direction and the side seal portions are easy to be torn off when the underpants-type disposable diaper is put off.

<The Invention of Claim 14>

A method for forming a stretchable structure for absorbent article, comprising: rotary driving a pleat formation roll with circumferentially continuous grooves in an outer peripheral surface of the pleat formation roll around a shaft center thereof and setting a continuous belt-like air permeable material around the outer peripheral surface of the pleat formation roll and passing the same in a rotating direction; supplying elongated resilient and elastic members in a line flow direction to the groove passage position of the air permeable material at an entry side of the pleat formation roll, while the air permeable material is set around the peripheral surface of the pleat formation roll and passed in the rotating direction; setting a line tension of the air permeable material at the entry side of the pleat formation roll as a line tension to generate a width reduction of the air permeable material; setting a line tension of the air permeable material at an exit side of the pleat formation roll as a line tension to return from the width reduction; decreasing the line tension on the pleat formation roll so that a portion of the air permeable material returned from the width reduction is put into the grooves under a line tension of the resilient and elastic members thereby forming pleat-like portions in the air permeable material; after that, joining pleat-like portions such that at least opposing surfaces of each pleat-like portion at a base portion are not separated; and fixing the resilient and elastic members, at least at portions to be both end portions of the resilient and elastic member, between the opposing surfaces of pleat-like portions after the supply of the resilient and elastic members.

(Operation and Effect)

The stretchable structure described in claim 1 and others can be manufactured by the foregoing method. The width reduction refers to the reduction of the width by the extension of the material in the line flow direction.

<The Invention of Claim 15>

The method for forming a stretchable structure for absorbent article according to claim 14, wherein a roll with circumferential changes in the depth of the grooves is used as the pleat formation roll to change protrusion height of the pleats in the line flow direction.

(Operation and Effect)

The stretchable structure according to claim 11 can be manufactured by the foregoing method.

<The Invention of Claim 16>

A method for forming a stretchable structure for absorbent article, comprising: bending an air permeable material to form pleats and cover portions overlapping a skin-side of the pleats in a fallen state; arranging elongated resilient and elastic members in an extended state to pass between base portions and tip portions of the pleats; fixing at least both end portions of the resilient and elastic members between opposing surfaces of the pleats; fixing continuously or intermittently the opposing surfaces of the pleats along an extending direction of the pleats such that the opposing surfaces of each pleat are not separated at the base portion of the pleat; and after that releasing the resilient and elastic members from the extended state to contract the pleats and the cover portions by contraction of the resilient and elastic members to form wrinkles in the pleats and the cover portions.

(Operation and Effect)

The stretchable structure according to claim 1 and others can be manufactured by the foregoing method.

Advantageous Effects of Invention

As described above, the present invention produces an advantage that it is possible to provide a stretchable structure allowing significant reduction in material cost, and others.

DESCRIPTION OF EMBODIMENTS

Embodiments of the present invention will be described below with reference to the accompanying drawings.

FIGS. 1 to 8 illustrate one example of underpants-type disposable diaper 100. The underpants-type disposable diaper 100 is composed of an outer body 12 constituting the outer surface (back surface) of the product and an inner body 200 stuck to the inner surface of the outer body 12. Reference sign Y indicates the entire length of the diaper, and reference sign X indicates the entire width of the diaper.

The inner body 200 is a portion absorbing and retaining excretion and the like such as urine, and the outer body 12 is a portion to be attached to the wearer. The dotted portions in the cross-sectional views indicate joined sections where constituent members are joined. The joined sections are formed by application of a hot-melt adhesive through solid, bead, curtain, summit, or spiral coating. In the following description, the "front-back direction" refers to the direction linking the ventral-side (front side) and the back side (rear side), and the "width direction" refers to the direction (right-left direction) orthogonal to the front-back direction. The "up-down direction" refers to the direction that becomes orthogonal to the waist direction when the diaper 100 is worn, that is, when the diaper 100 is folded into two at the crotch portion such that the front body part and the back body part are overlapped at the both sides, in other words, the direction linking a waist opening WO and a crotch portion.

(Inner Body)

Figure 1:
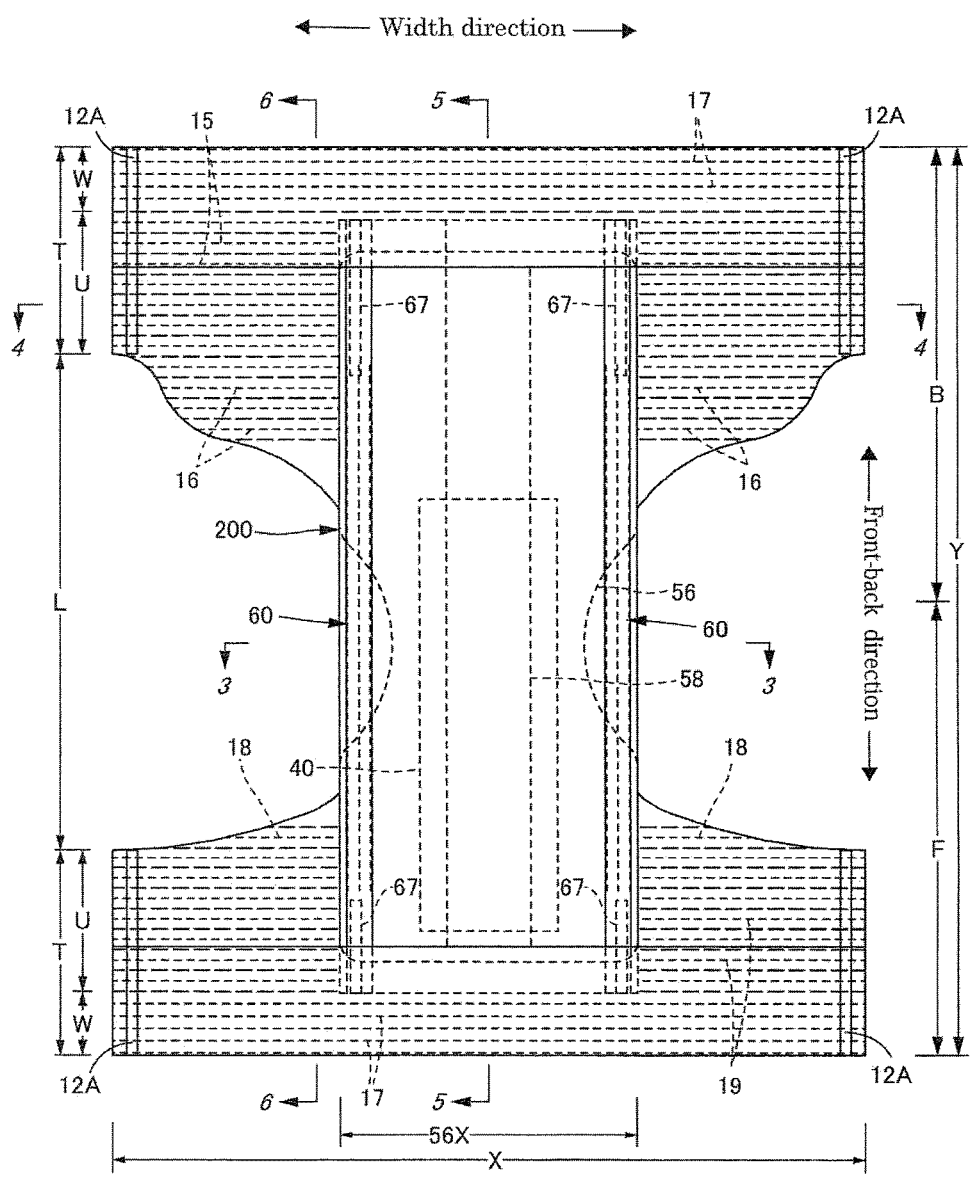
FIG. 1 is a planar view of an inner surface of an underpants-type disposable diaper in the open state.
Figure 2:
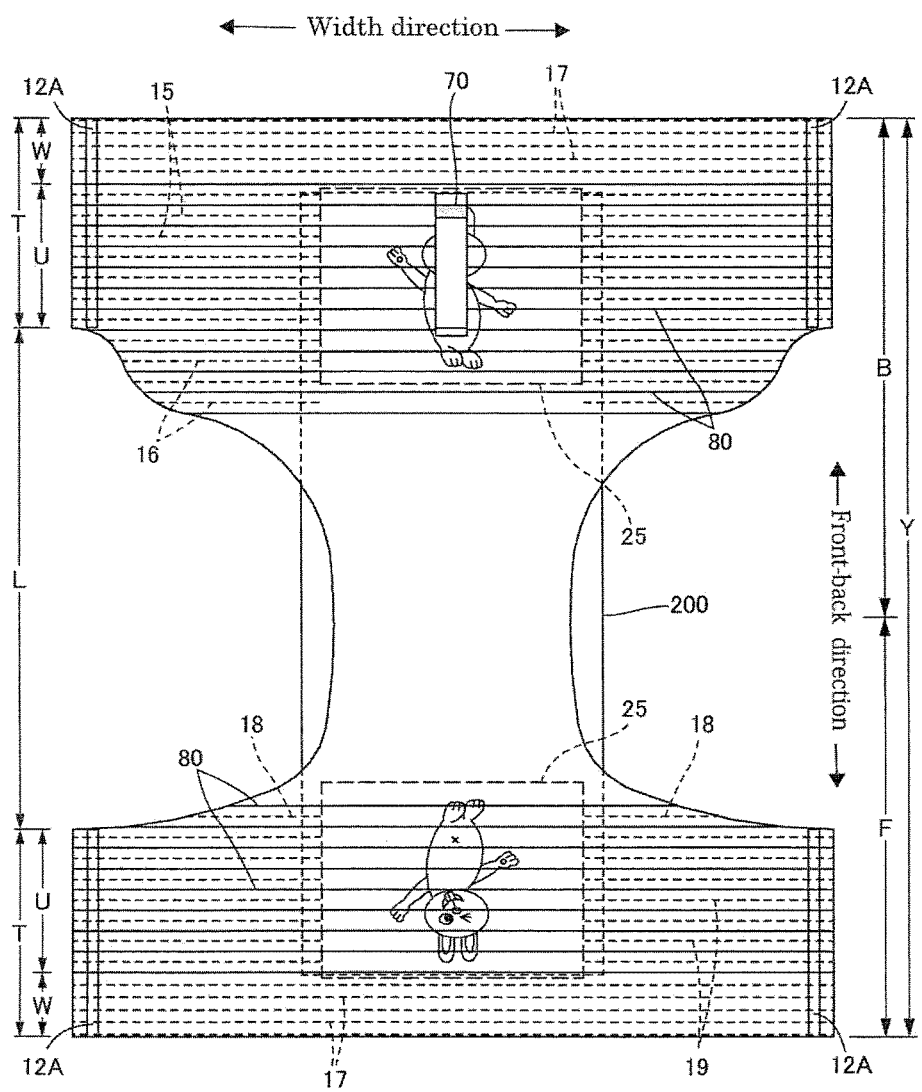
FIG. 2 is a planar view of an outer surface of the underpants-type disposable diaper in the open state.
Figure 3:
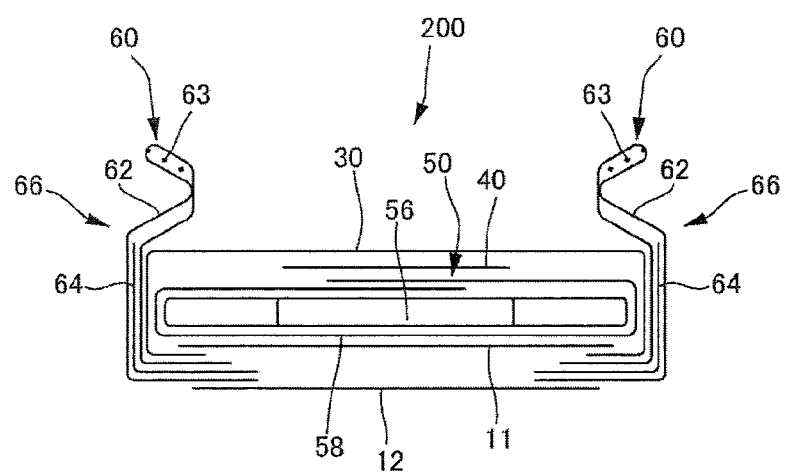
FIG. 3 is a cross-sectional view of FIG. 1 taken along line 3-3.
Figure 4:
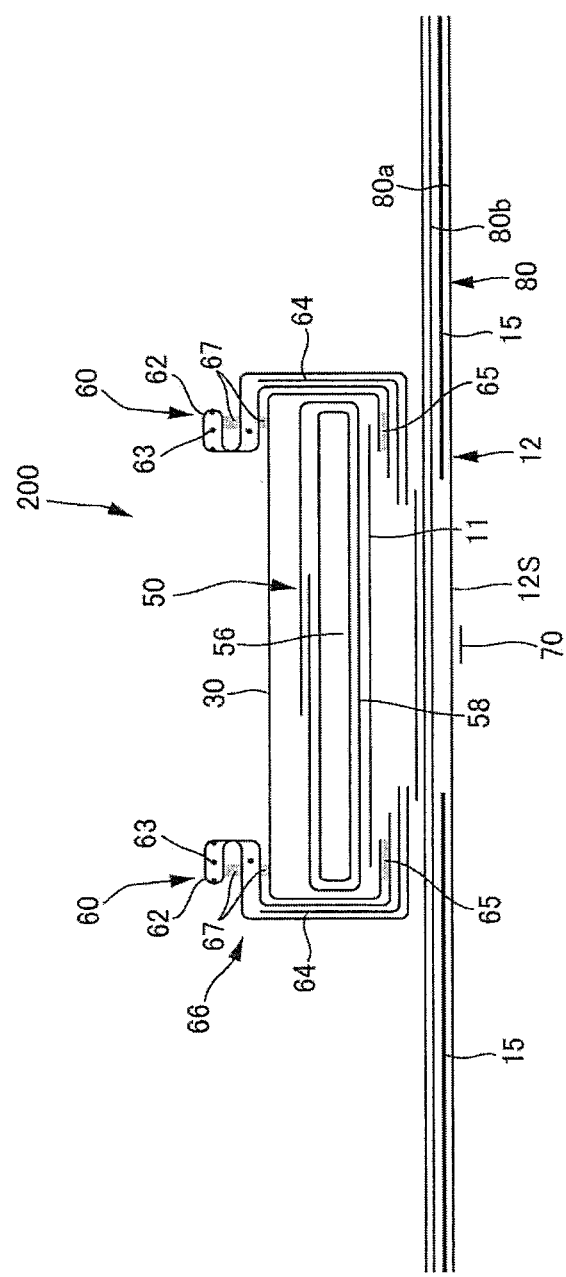
FIG. 4 is a cross-sectional view of FIG. 1 taken along line 4-4.
Figure 5:
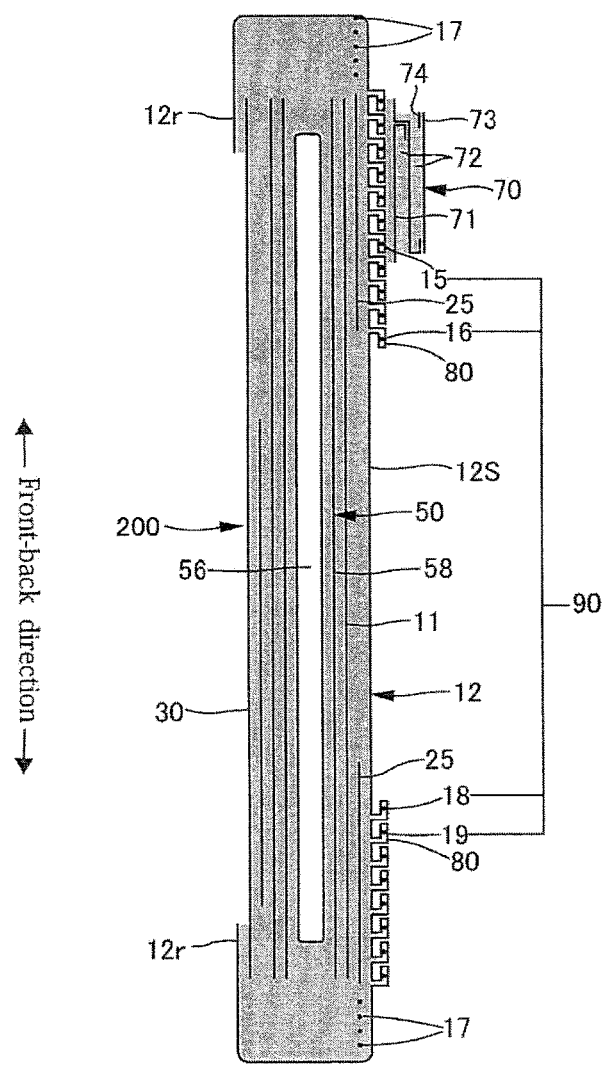
FIG. 5 is a cross-sectional view of FIG. 1 taken along line 5-5.

The inner body 200 may be formed in any shape, although it is rectangular in the illustrated mode. The inner body 200 is a main body part with absorptive function that includes a face sheet 30 on the wearer's body side, a liquid impervious sheet 11, and an absorbent element 50 intervening between these sheets as illustrated in FIGS. 3 to 5. Reference sign 40 indicates an interlayer sheet (second sheet) provided between the face sheet 30 and the absorbent element 50 to move quickly the liquid having passed through the face sheet 30 to the absorbent element 50. Reference sign 60 indicates three-dimensional gathers 60 standing from the both sides of the inner body 200 toward the wearer's body to prevent excretion from leaking toward the both sides of the inner body 200.

(Face Sheet)

The face sheet 30 is pervious to liquid and may be a porous or non-porous non-woven fabric sheet or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The face sheet 30 may be composed of a single sheet or a layered sheet obtained by sticking two or more sheets to each other. Similarly, the face sheet 30 may be composed of a single sheet or two or more sheets in a planar direction.

In the case of providing the three-dimensional gathers 60, it is preferred that the both sides of the face sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.

(Interlayer Sheet)

To move the liquid having passed through the face sheet 30 quickly to the absorber, the interlayer sheet (also called as "second sheet") 40 higher in liquid permeation speed than the face sheet 30 may be provided. The interlayer sheet 40 can not only move the liquid quickly to the absorber with enhancement in absorption performance of the absorber but also prevent a "back-flow" phenomenon of the absorbed liquid from the absorber to keep the face sheet 30 in a dry state. The interlayer sheet 40 may not be provided.

The interlayer sheet 40 may be made from the same material as that for the face sheet 30, or spun-laced, spun-bonded, SMS, or pulp non-woven fabric, or mixture of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 $g/m^2$, more preferably 25 to 60 $g/m^2$. The thickness of raw fibers for the non-woven fabric is preferably 2.2 to 10 dtex. To increase the bulk of the non-woven fabric, all or some of the raw fibers are preferably eccentric fibers with cores not centered, hollow fibers, or eccentric and hollow fibers.

The interlayer sheet 40 in the illustrated mode is centered on an absorber 56 and is narrower than the absorber 56. Alternatively, the interlayer sheet 40 may be provided over the entire width of the absorber 56. The interlayer sheet 40 may be the same in length as the absorber 56, or may be shorter than the absorber 56, falling within the central area for receiving the liquid.

(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric is laid on a plastic film, or the like. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filling agent in an olefin resin such as polyethylene, polypropylene, and the like to form a sheet and then elongating the sheet in a uniaxial or biaxial direction. Besides, the liquid impervious sheet 11 may be a non-woven fabric of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the face sheet 30-side. The appropriate width of the extended portions is about 5 to 20 mm at each of the right and left sides.

An excretion indicator changed in color by absorption of liquid may be provided at the inside of the liquid impervious sheet 11, in particular, on the side surfaces of the absorber 56.

(Three-dimensional Gathers)

The three-dimensional gathers 60 are belt-shaped members extended entirely along the both sides of the inner body 200 in the front-back direction. The three-dimensional gathers 60 are provided to shut off urine or loose stool moving laterally over the face sheet 30 to prevent lateral leakage of the liquid. In this embodiment, the three-dimensional gathers 60 stand on the sides of the inner body 200. Each of the three-dimensional gathers 60 stands obliquely toward the central portion in the width direction at the base side, and stands obliquely toward the outside in the width direction from the middle portion to the edge portion.

More specifically, each of the three-dimensional gathers 60 is formed such that a belt-shaped gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at the folded portion and its neighborhood. The end portions of the three-dimensional gathers 60 at the sides opposite to the folded portions in the width direction constitute attachment portions 65 fixed to the back surface of the inner body 200 at the side edges. The portions of the three-dimensional gathers 60 other than the attachment portions 65 constitute protrusions 66 (folded portions) that protrude from the attachment portions 65. The both ends of the protrusions 66 in the front-back direction include base portions that are extended from the attachment portions 65 through the sides of the inner body 200 to the side surfaces of the face sheet 30 and are fixed by front-back fixed portions 67 with a hot-melt adhesive or a heat seal to the side surfaces of the face sheet 30, and edge portions that are folded back from the edges of the base portions toward the outside in the width direction and are fixed to the base portions. The middle portions of the protrusions in the front-back direction are non-fixed free portions (inner free portions) to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m². The elongated resilient and elastic members 63 may be rubber threads or the like. In the case of using spandex rubber threads, the thickness of the threads is preferably 200 to 1240 dtex, more specifically 620 to 940 dtex. The extension ratio of the threads at the time of fixing is preferably 150 to 350%, more specifically 200 to 300%. The "extension ratio" herein takes on a value relative to the natural length as 100%. In addition, a water-proof film 64 may intervene in the gather sheet folded in two as illustrated in the drawing.

The number of the elongated resilient and elastic members 63 provided in the free portions of the three-dimensional gathers 60 is preferably two to six, more specifically three to five. The arrangement interval 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the face sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact with the circumferences of the legs to produce an improved fit.

Figure 7:
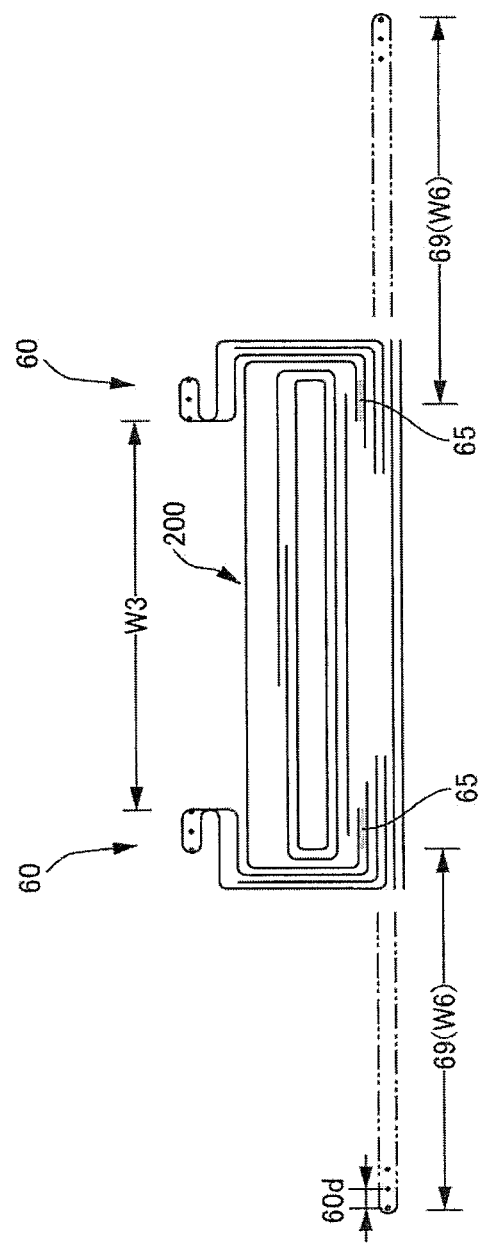
FIG. 7 is a cross-sectional view of three-dimensional gathers in the open state.

The dimensions of the three-dimensional gathers 60 can be decided as appropriate. In the case of a disposable diaper for infants, however, the standing height 66w of the three-dimensional gathers 60 (width of the protrusions 66 in an open state) is preferably 15 to 60 mm, more specifically 20 to 40 mm as illustrated in FIG. 7, for example. In addition, the separation distance 60d between the folds at the innermost side in the flatly folded state is preferably 60 to 190 mm, more specifically 70 to 140 mm, to make the three-dimensional gathers 60 parallel to the surface of the top sheet 30.

Unlike in the illustrated mode, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluffy pulp or accumulated short fibers may be about 100 to 300 g/m², and the basis weight of a filament assembly may be about 30 to 120 g/m², for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

Figure 6:
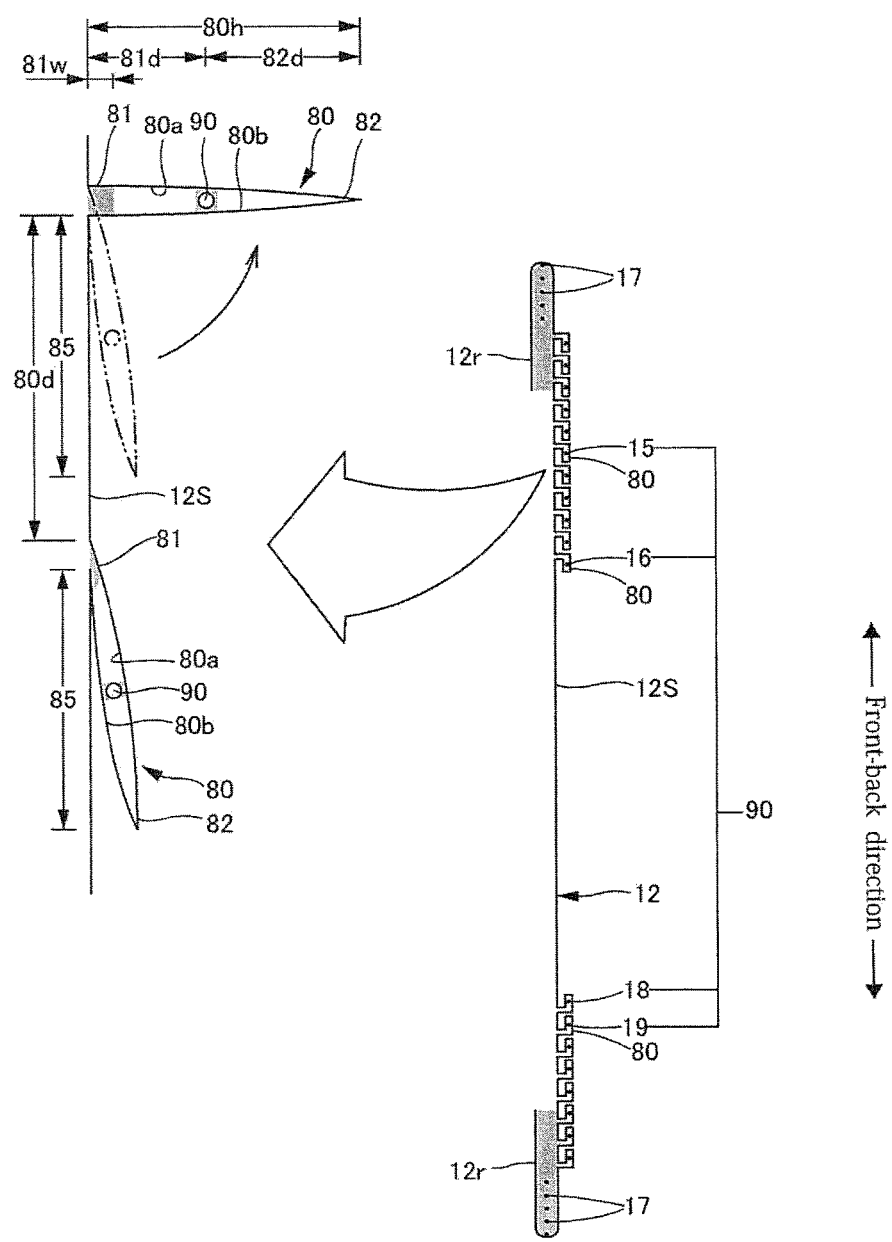
FIG. 6 is a cross-sectional view of FIG. 1 taken along line 6-6.

The absorber 56 may be rectangular in shape but preferably has a hourglass shape having a front end portion, a back end portion, and a narrower portion that is positioned between the front and back end portions and is narrower than the two end portions as illustrated in FIG. 6 to improve the absorber 56 and the three-dimensional gathers 60 in a fit to the circumferences of the legs.

The dimensions of the absorber can be decided as appropriate. Nevertheless, the absorber preferably extends to the peripheral edges or their neighborhoods of the inner body in the front-back direction and the width direction. Reference sign 56X indicates the width of the absorber 56.

(High-absorbent Polymer Particles)

The absorber 56 may partially or entirely contain high-absorbent polymer particles. The high-absorbent polymer particles include "particles" and "powder". The diameter of the high-absorbent polymer particles may be the same as that of particles for general use in this type of absorbent article, and is desirably 1000 μm or less, in particular 150 to 400 μm. There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylate graft copolymer, a saponified material of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 40 seconds or less. At a water absorption rate of more than 40 seconds, the absorbed liquid is more likely to flow back from the absorber 56 to the outside of the absorber 56 (so called "back-flow").

The gel strength of the high-absorbent polymer particles is preferably 1000 Pa or more. Accordingly, it is possible to suppress effectively a sticky feeling of the absorber 56 after liquid absorption even when the absorber 56 is of high bulk.

The basis weight of the high-absorbent polymer particles can be decided as appropriate according to the absorbing capability required for the use of the absorber 56. Although not definitely specified, the basis weight may be 50 to 350 g/m$^2$. When the basis weight of the polymer is less than 50 g/m$^2$, it is difficult to provide the necessary absorbing capability. When the basis weight of the polymer exceeds 350 g/m$^2$, the absorbing effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion area than the other areas. With regard to gender differences, the dispersing density (quantity) of the high-absorbent polymer particles may be increased at the front side of the product for male, and may be increased at the central part of the product for female. In addition, the polymer may not be provided locally (in spots) in the absorber 56 in the planar direction.

(Wrapping Sheet)

The material for the wrapping sheet 58 may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of manufacture and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the front and back sides of the absorber 56 so that the extended portions are crushed on the front and back sides and joined by a joint means such as a hot-melt adhesive.

(Outer Body)

Figure 8:
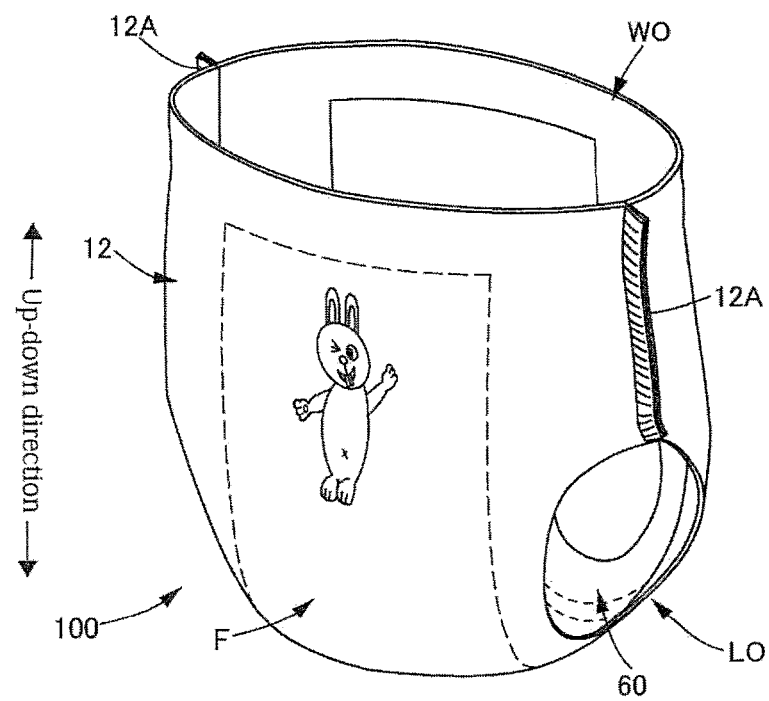
FIG. 8 is a perspective view of the underpants-type disposable diaper.

The outer body 12 has a part constituting a front body part F extended from the crotch portion to the ventral-side and a part constituting a back body part B extended from the crotch portion to the back side. The front body part F and the back body part B are joined at the both sides to form a waist opening WO through which the wearer's waist is passed and a pair of right and left leg openings LO through which the wearer's legs are passed as illustrated in FIG. 8. Reference sign 12A indicates joined sections (hereinafter, also referred to as side seal portions). The crotch portion refers to a central portion in the front-back direction from the waist edge of the front body part F to the waist edge of the back body part B in an open state. The portions on the front side and the back side of the crotch portion refer to the front body part F and the back body part B, respectively.

The outer body 12 has waist portions T determined as front-back areas from the waist opening WO to the upper ends of the leg openings LO, and an intermediate portion L determined as a front-back area forming the leg openings LO (between the front-back area having the side seal portions 12A of the front body part F and the front-back area having the side seal portions 12A of the back body part B). The waist portions T are conceptually divided into "waist edge portions" W forming the edge of the waist opening and "waist lower portions" U as the portions under the waist edge portions W. The lengths of these portions in the vertical direction vary depending on the size of the product and can be decided as appropriate. As an example, the length of the waist edge portion W may be 15 to 40 mm, and the length of the waist lower portion U may be 65 to 120 mm. The both ends of the intermediate portion L are narrowed along the circumferences of the wearer's legs, and the wearer's legs are placed through the narrowed ends. As a result, the outer body 12 has an almost hourglass shape as a whole. The degree of narrowing of the outer body 12 can be decided as appropriate. As in the modes illustrated in FIGS. 1 to 8, the outer body 12 is preferably narrower than the inner body 200 at the narrowest area for simple appearance. Alternatively, the outer body 12 may be wider than the inner body 200 even at the narrowest area.

The outer body 12 illustrated in FIGS. 3 to 6 is formed by attaching elongated resilient and elastic members 90 to one sheet material 12S. The outer body 12 is folded back inside at the edge of the wait opening, and a folded portion 12r is extended to cover the upper end portion of the inner body 200 at the waist side.

There is no particular limitation on the sheet material 12S as far as it is an air permeable sheet, but it is preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example.

In the outer body 12, the elongated (thread-like or band-like) resilient and elastic members 90 (resilient and elastic members 15 to 19) are attached to the sheet material 12S to enhance the fit to the wearer's waist. The resilient and elastic members 90 may be formed from synthetic rubber or natural rubber.

More specifically, in the folded portion 12r of the sheet material 12S at the waist edge portions W of the back body part B and the front body part F, a plurality of waist edge resilient and elastic members 17 is fixed at least at both end portions in the extended state along the width direction at a predetermined extension ratio with spacing therebetween in the up-down direction in such a manner as to be entirely continuous in the width direction. One or more of the waist edge resilient and elastic members 17 in the area adjacent to the waist lower portions U may overlap the inner body 200 or may be provided at the both sides of the middle portion in the width direction overlapping the inner body 200. As the waist edge resilient and elastic members 17, about 3 to 22 resilient and elastic members with a fineness of 155 to 1880 dtex, in particular about 200 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 150 to 400%, in particular about 220 to 320%, with spacing of 4 to 12 mm. All of the waist edge resilient and elastic members 17 may not be equal in fineness and extension ratio. For example, the resilient and elastic members may be different in fineness and extension ratio between the upper and lower sides of the waist edge portions W.

In the waist lower portions U of the front body part F and the back body part B, a plurality of waist lower portion resilient and elastic members 15 and 19 is fixed at least at both end portions in the extended state in the width direction at a predetermined extension ratio with spacing therebetween in the up-down direction in such a manner as to be entirely continuous in the width direction, at sections at the upper side and both sides of the middle portion in the width direction overlapping the inner body 200.

As the waist lower portion resilient and elastic members 15 and 19, about 5 to 30 resilient and elastic members with a fineness of 155 to 1880 dtex, in particular about 200 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 200 to 350%, in particular about 240 to 300%, with spacing of 1 to 15 mm, in particular 3 to 8 mm.

In the intermediate portion L between the front body part F and the back body part B, a plurality of intermediate portion resilient and elastic members 16 and 18 composed of elongated resilient and elastic members is fixed at least at both end portions in the extended state along the width direction at a predetermined extension ratio with spacing therebetween in the up-down direction in such a manner as to be entirely continuous in the width direction, at the both sides of the middle portion in the width direction overlapping the inner body 200.

As the intermediate portion resilient and elastic members 16 and 18, about 2 to 10 resilient and elastic members with a fineness of 155 to 1880 dtex, in particular about 200 to 1240 dtex (this is applied in the case of a synthetic rubber, and in the case of a natural rubber, a cross-section area of 0.05 to 1.5 mm$^2$, in particular about 0.1 to 1.0 mm$^2$) are preferably fixed at an extension ratio of 150 to 300%, in particular about 180 to 260%, with spacing of 5 to 40 mm, in particular 5 to 20 mm.

When the waist lower portion resilient and elastic members 15 and 19 and the intermediate portion resilient and elastic members 16 and 18 are provided at the both sides of the middle portion in the width direction overlapping the inner body 200 as illustrated in the drawings, the inner body 200 does not contract more than necessary in the width direction, or become lumpy with deterioration in appearance, or decrease in absorbing performance. The foregoing form includes the form in which the resilient and elastic members 15, 16, 18, and 19 reside only at the both sides in the width direction, and the form in which the resilient and elastic members 15, 16, 18, and 19 reside crossing over the inner body 200 from one to the other sides in the width direction, but the resilient and elastic members 15, 16, 18, and 19 are finely cut and exert no contraction force at the middle portion in the width direction overlapping the inner body 200 (this substantially means that no resilient and elastic members 15, 16, 18, and 19 are provided), and thus the contraction force of the resilient and elastic members 15, 16, 18, and 19 acts only at the both sides in the width direction. The cross-sectional view of FIG. 5 illustrates the finely cut resilient and elastic members 15, 16, 18, and 19, but the planar view does not illustrate the same. As a matter of course, the arrangement forms of the waist lower portion resilient and elastic members 15 and 19 and the intermediate portion resilient and elastic members 16 and 18 are not limited to the foregoing ones. Alternatively, some or all of the waist lower portion resilient and elastic members 15 and 19 and the intermediate portion resilient and elastic members 16 and 18 may be provided crossing over the inner body 200 from the one to the other sides in the width direction so that the contraction force acts on the entire waist lower portions U in the width direction.

(Outer Body Separation Structure)

Figure 12:
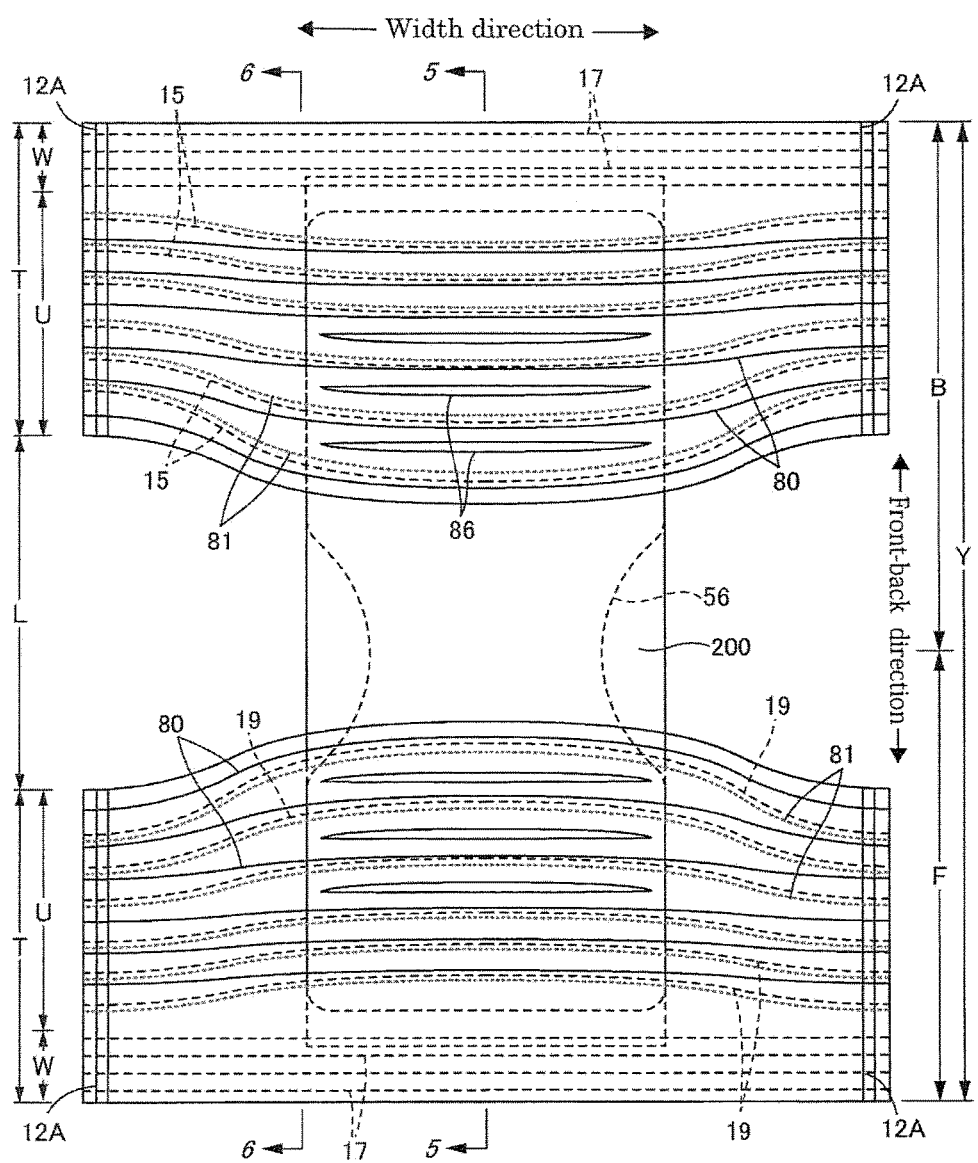
FIG. 12 is a planar view of an outer surface of an underpants-type disposable diaper in the open state.
Figure 13:
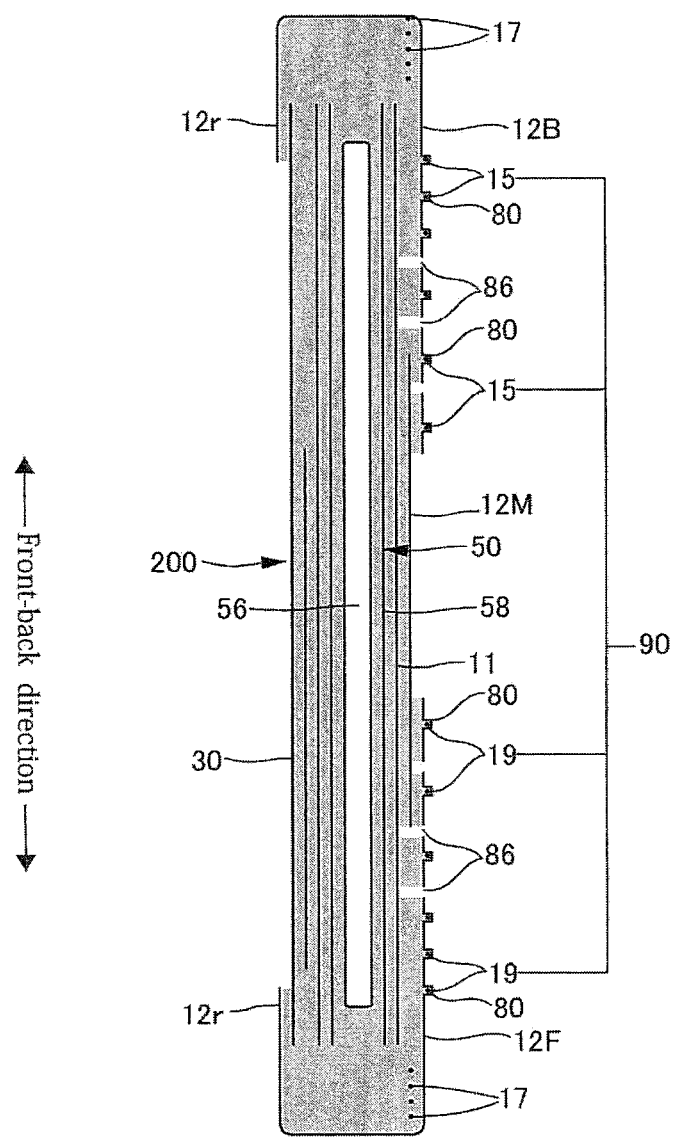
FIG. 13 is a cross-sectional view of FIG. 12 taken along line 5-5.
Figure 14:
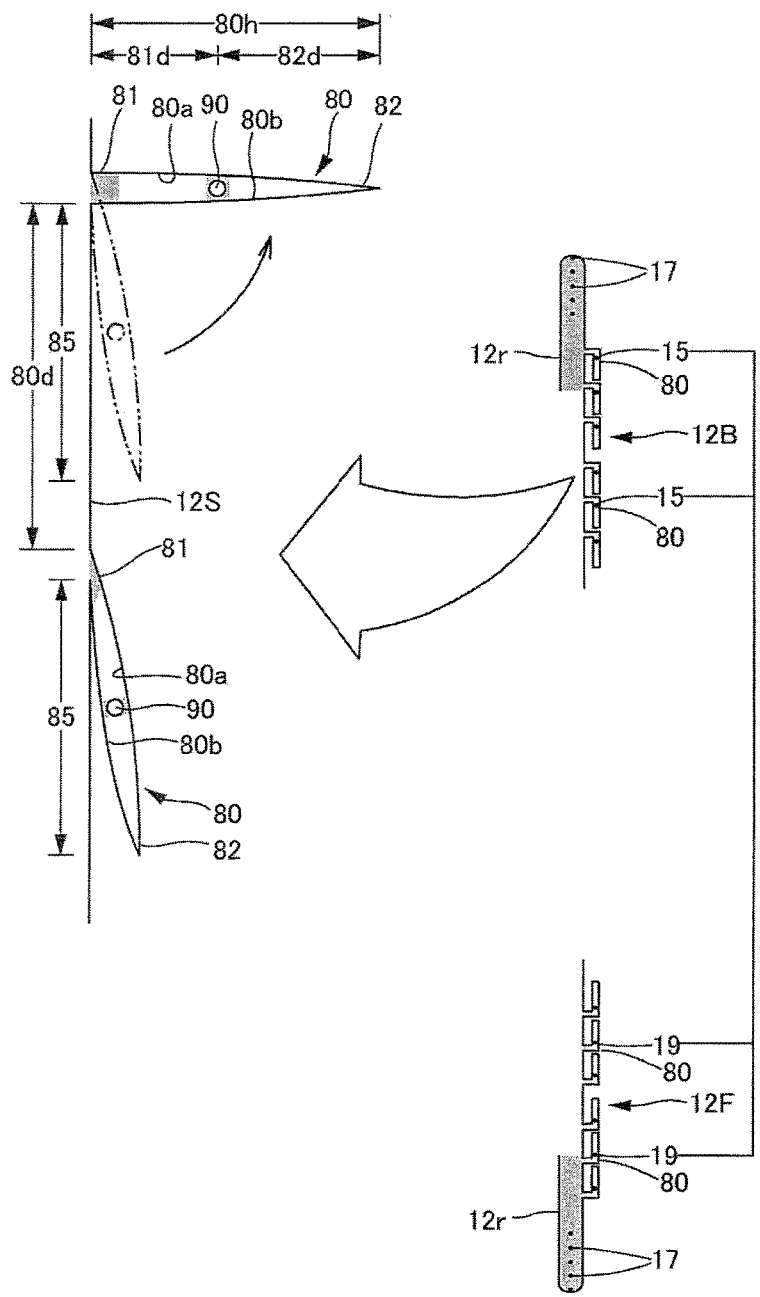
FIG. 14 is a cross-sectional view of FIG. 12 taken along line 6-6.
Figure 15:
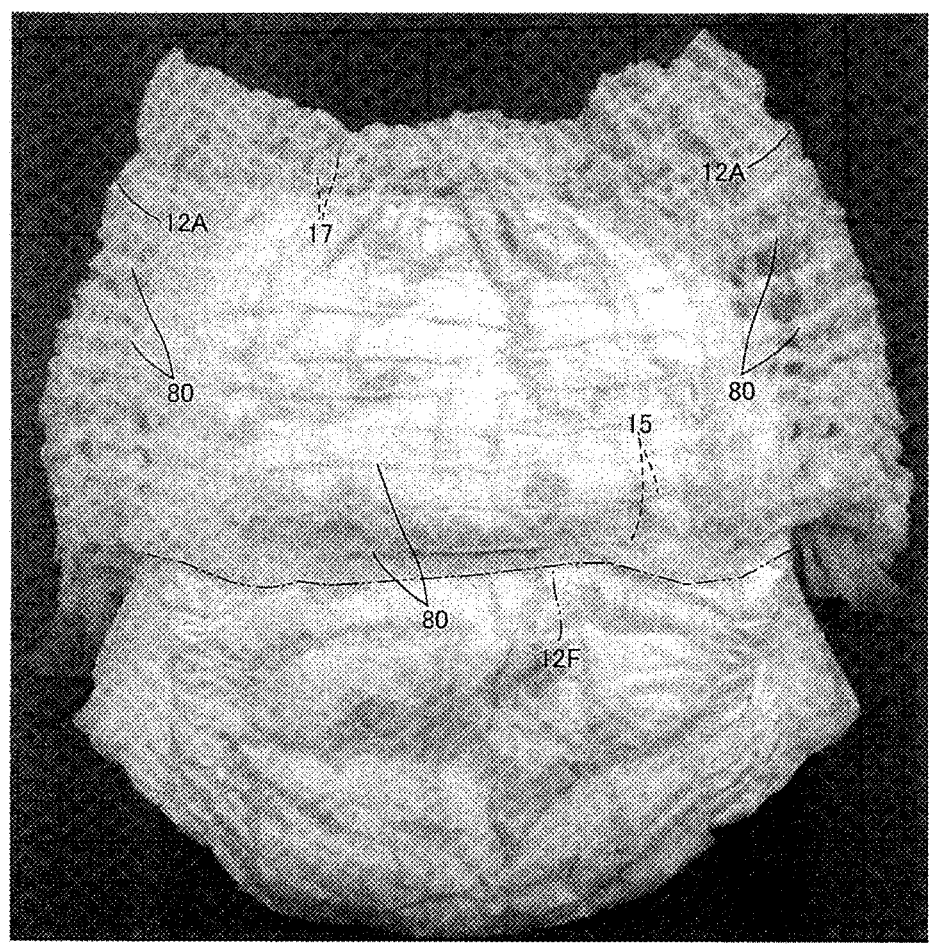
FIG. 15 is a photograph of a sample.

In the foregoing example, the integral outer body 12 covers continuously from the front body part F to the back body part B. Alternatively, as illustrated in FIG. 12, the front outer body 12F constituting the ventral-side and the back outer body 12B constituting the back side may be discontinued and spaced from each other at the crotch-side. In that case, a crotch portion outer body 12M may be stuck to the outer surface of the inner body 200 to cover the portion exposed between the front outer body 12F and the back outer body 12B. For the crotch portion outer body 12M, the same material as that for the foregoing outer body 12 can be used.

(Post-treatment Tape)

A post-treatment tape 70 (fixing means) can be provided on the outer surface of the back body part B of the outer body 12 at the central portion in the width direction. The post-treatment tape 70 is intended to fasten the rolled or folded diaper 100 such that the face sheet 30 and the front body part F are positioned inside. In general, the post-treatment tape 70 has a base end portion 71 fixed to the outer surface of the outer body 12 by an adhesive or the like, a portion of the post-treatment tape 70 at the tip-side with regard to the base end portion 71 is folded in three (with a Z-shaped cross section) or two, and the folded and overlapped portions are (tentatively) fixed to each other by a tentative adhesive 72 in such a manner as to be capable of being unfixed as illustrated in FIG. 5. The post-treatment tape 70 also has a tab 73 colored in an opaque color such as white at the tip portion. The portion of the post-treatment tape 70 other than the tab 73 is transparent or translucent. A design described later is viewable from the outer surface-side of the post-treatment tape 70 through the transparent or translucent portion of the post-treatment tape 70. Specific structure of the post-treatment tape 70 may be determined as appropriate. In the illustrated mode, the post-treatment tape 70 is entirely formed by coupling a plurality of transparent or translucent base materials in a longitudinal direction, and a colored tape 74 is stuck to the tab 73.

To discard the diaper 100, the diaper 100 is rolled or folded such that the face sheet 30 and the front body part F are positioned inside, the folded and overlapped portions of the post-treatment tape 70 are unfixed and extended to wrap around the rolled or folded diaper 100 from the back body part B through the waist opening WO to the outer surface of the opposite side, and then is fixed by the adhesive. In particular, the post-treatment tape 70 is preferably a three-folded type so that the post-treatment tape 70 can be folded in a compact size when being not used and can be extended in a rectangular shape when being used.

The fixing means such as the post-treatment tape 70 may be provided at the front body part F or at both the back body part B and the front body part F.

(Printed Sheets)

Printed sheets 25 with printed designs are provided between the liquid impervious sheet 11 and the outer body 12. The outer body 12 may not be provided to expose the printed sheets 25 on the outer surface. The printed sheets 25 in the illustrated example are smaller in area than the body parts on which they are arranged, and are individually provided on the front body part F and the back body part B. Alternatively, the printed sheet 25 may be continuously provided from the front body part F through the crotch portion to the back body part B.

There are no particular limitations on the dimensions and shape of the printed sheets 25. However, it is preferred that the printed sheets 25 are sufficiently large in area to be fully functional. For example, the width of the printed sheets 25 is preferably about 50 to 120% of the width of the absorber 56, and the length of the printed sheets 25 is preferably about 15 to 30% of the article entire length Y at least at one of the ventral-side and the back side. The shape of the printed sheets 25 is preferably rectangular as in the illustrated example in terms of eliminating trim loss, but the printed sheets 25 may be cut in any other geometric shape such as circle, oval, triangle, or hexagon, or in any shape along the periphery of the design.

The sheet base material for the printed sheets 25 may be a plastic film, non-woven fabric, paper, or the like, but is preferably less bulky and highly air-permeable material. The plastic film is desirably moisture permeable due to prevention of stuffiness. The non-woven fabric and paper are preferred for their moisture permeability. To provide some printed design, the non-woven fabric is preferably high in smoothness for easy printing, and the paper is preferably high in strength to make ink blurring less prone to occur. Preferred in particular are crape paper (thin paper) with a basis weight of about 15 to 35 g/m$^2$ and a thickness of about 0.1 to 0.3 mm, and non-woven fabric (specifically, spun-bonded non-woven fabric or SMS non-woven fabric with a fineness of about 1.0 to 3.0 dtex at a spun-bonded portion) with a basis weight of about 10 to 25 g/m$^2$ and a thickness of 0.1 to 0.3 mm. The crape paper preferably has a crape ratio of about 5 to 20%, in particular about 5 to 15%. The crape paper with a crape ratio of 20% or more is not suitable for design printing because a larger amount of ink is fixed but blurred. The crape paper with a crape ratio of 5% or less has an insufficient ink penetration, thereby resulting in a smaller amount of ink fixation.

(Stretchable Structure)

Figure 9:
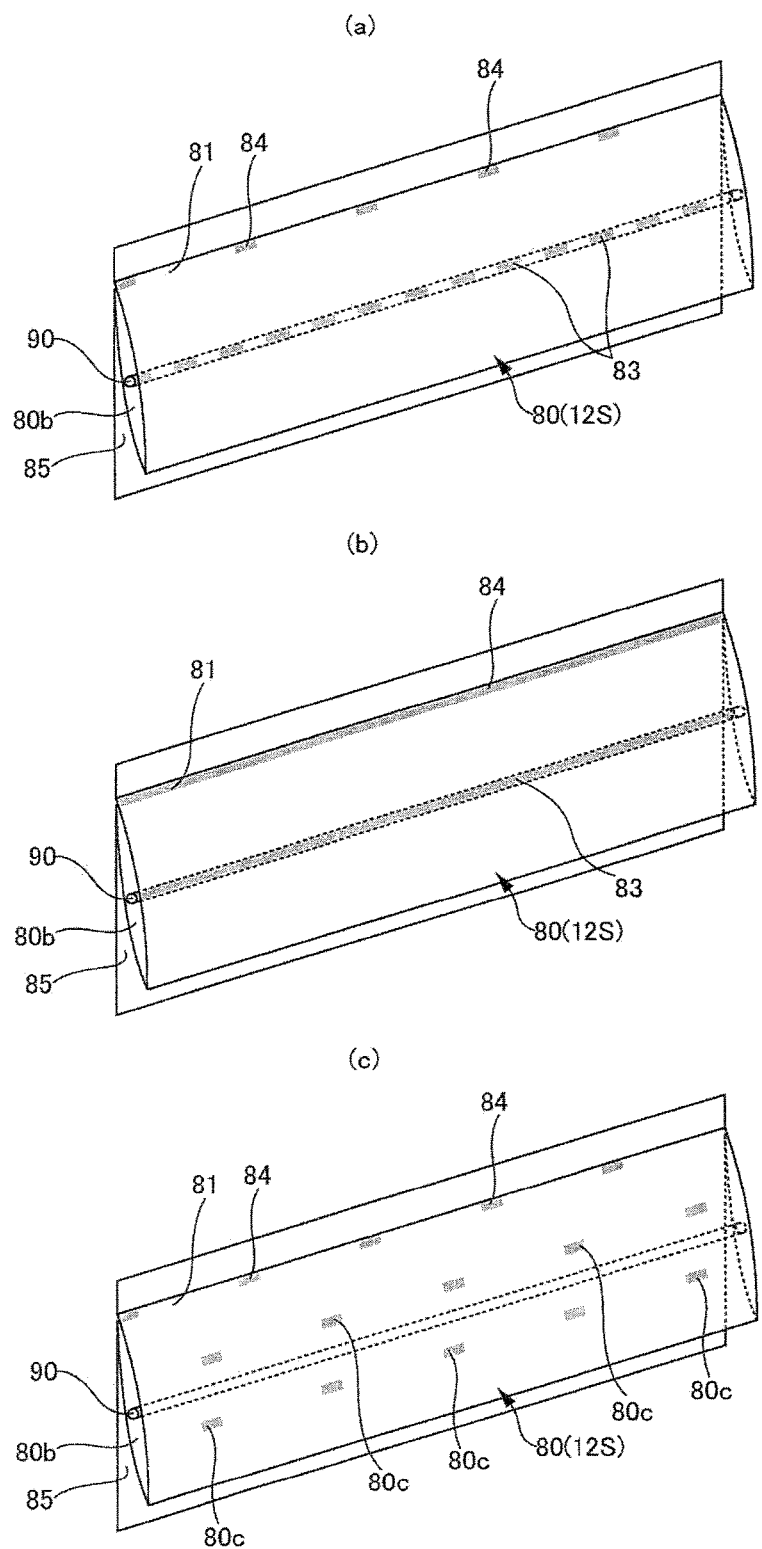
FIG. 9 is a perspective view of a stretchable structure.

In the underpants-type disposable diaper, a stretchable structure of the present invention is employed in the area ranging from the waist lower portions U to the intermediate portion L. Specifically, as illustrated in FIGS. 6 and 9, the underpants-type disposable diaper includes: the sheet-like member 12S that has a large number of pleats 80 protruding toward the side opposite to the skin-contact-side and arranged at vertical intervals so as not to overlap each other in a fallen state and inter-pleat portions 85 (cover portions) overlapping the pleats 80 at the skin-side in the fallen state; and elongated resilient and elastic members 90 (resilient and elastic members 15, 16, 18, and 19) provided along the longitudinal direction of the pleats 80 between the opposing surfaces 80*a* and 80*b* of the pleats 80. The resilient and elastic members 90 are arranged to pass through the pleats at the tip-side with regard to the base portions 81, and are fixed at least at both end portions between the opposing surfaces 80*a* and 80*b* of the pleats 80. In addition, the opposing surfaces 80*a* and 80*b* of the pleats 80 are continuously or intermittently fixed along the extending direction of the pleats 80 such that the opposing surfaces 80*a* and 80*b* of each pleat 80 at the base portion 81 are not separated (not opened). Further, the outer surfaces of pleats 80 are not joined to the inter-pleat portion 85 except for the both end portions of the pleats 80 in the longitudinal direction. The pleats 80 and the inter-pleat portions 85 are contracted by the contraction of the resilient and elastic members 90 to form their wrinkles.

By forming the pleats 80 in the one air permeable material 120 and providing the resilient and elastic members 90 in the pleats 80, the material cost can be significantly reduced as compared to the case with the conventional structure in which the resilient and elastic members 90 are sandwiched between two air permeable materials 120. In addition, although the number of the overlapping materials is three or more at sections where the fallen pleats 80 overlap the inter-pleat portions 85, the pleats 80 and the inter-pleat portions 85 are not joined but air permeable gaps are formed between the pleats and the inter-pleat portions by their contraction wrinkles to suppress reduction in flexibility and air permeability.

Figure 10:
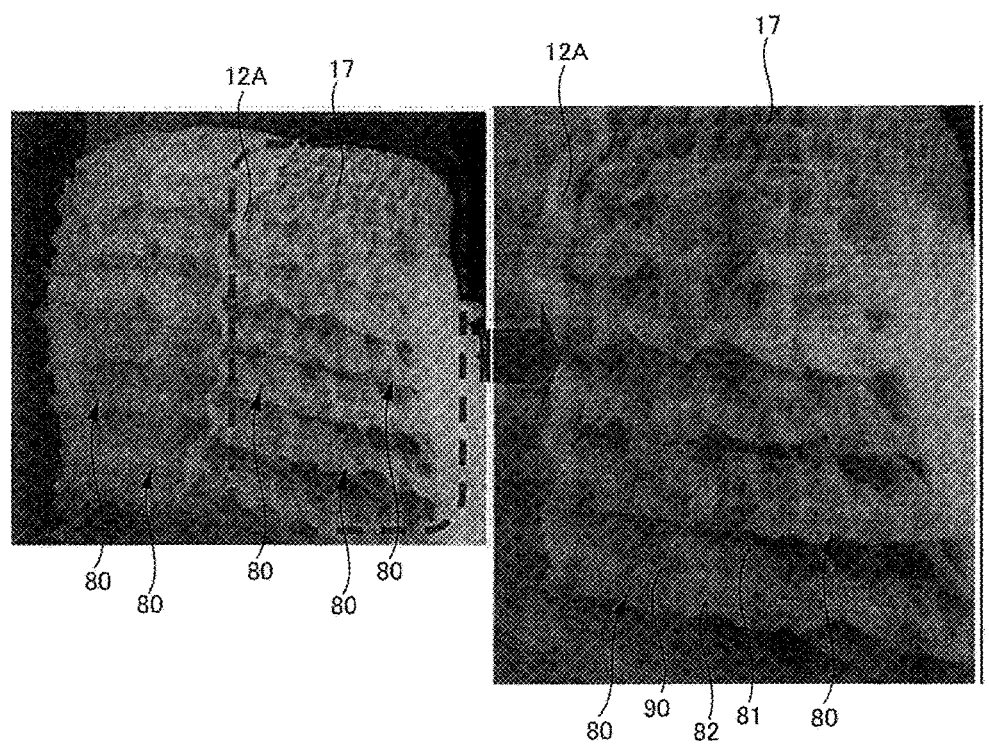
FIG. 10 represents photographs of a sample.
Figure 11:
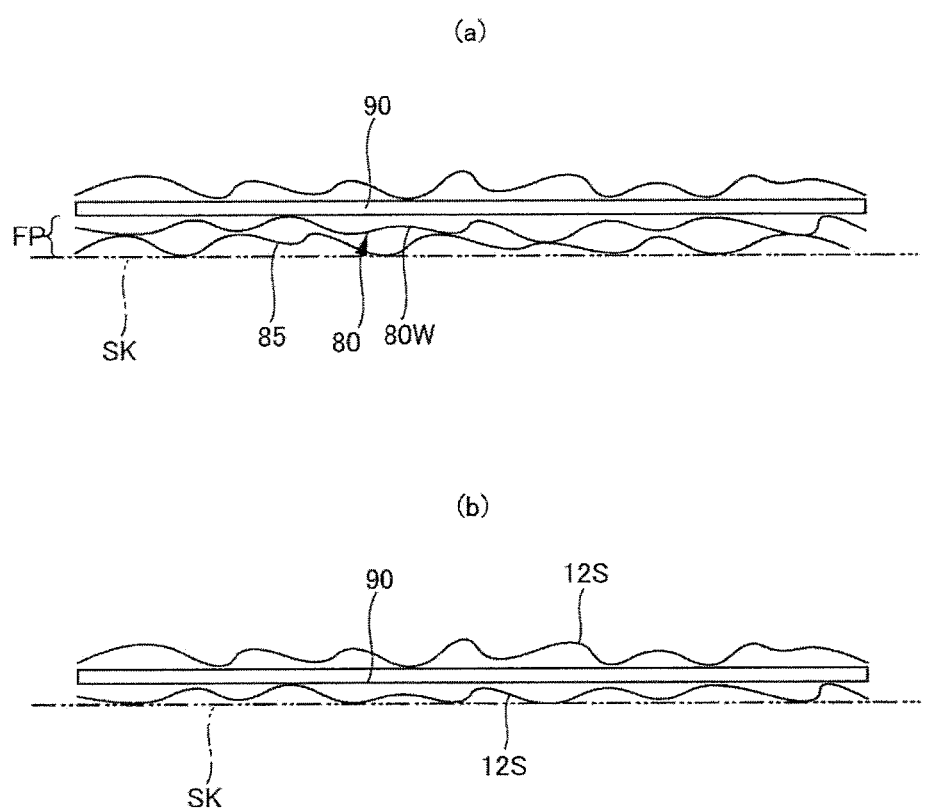
FIG. 11 is a schematic view illustrating a tightening reduction principle.

FIG. 10 represents photographs of main components of a prototype of a diaper (of the same structure as that of the embodiment) on a dummy, which shows wrinkles and the passage positions of the resilient and elastic members 90 in the diaper in the worn state. FIG. 11(*a*) schematically illustrates the cross section of the prototype in the worn state, and FIG. 11(*b*) schematically illustrates the cross section of a conventional diaper in the worn state in which the resilient and elastic members 90 are merely sandwiched between the two sheet-like materials 12S. The lines indicated with reference sign SK in the drawing represent the presumed skin surface of the wearer. As seen from these examples, in the stretchable structure of the present invention, the pleats 80 are tightened and fallen by the contraction of the resilient and elastic members 90, and skin-side wall portions 80W of the fallen pleats 80 and the inter-pleat portions 85 are positioned at the skin-sides of the resilient and elastic members 90 and increase in thickness by their respective contraction wrinkles. In particular, on the interval portions between the pleats 80 constituting the inter-pleat portions 85, the contraction force of the resilient and elastic members 90 at the both ends of the interval portions also acts, thereby producing firm wrinkles in the interval portions between the pleats 80. As compared to the conventional diaper illustrated in FIG. 11(*b*), highly cushioned thick portions FP are formed on the skin sides of the resilient and elastic members 90. The skin-side wall portions 80W of the pleats 80 become thicker at the base portion 81-sides and the tip portion 82-sides of the resilient and elastic members 90 by their respective contraction wrinkles, and the tightening force of the resilient and elastic members 90 is distributed to the base portion 81-sides and the tip portion 82-sides of the pleats 80. Accordingly, even though the resilient and elastic members 90 are positioned at the skin-side with regard to the base portions 81 and the tip portions 82, it is possible to suppress concentration of the tightening force. As a result, the tightening marks of the resilient and elastic members 90 are unlikely to be left on the skin. In addition, at the thick portions FP, the sheet-like members 12S are not closely adhered to each other but a large number of air permeable gaps are formed by the contraction wrinkles, thereby suppressing reduction in air permeability. Accordingly, in the stretchable structure of the present invention, it is possible to provide compatibility between prevention of reduction in air permeability and prevention of the tightening marks of the elongated resilient and elastic members 90.

The passage positions of the resilient and elastic members 90 in the pleats 80 merely need to be the tip-side with regard to the base portions 81 of the pleats 80. As in the example of FIG. 9, to form a certain clearance between the inner surface of the pleat 80 and the outer surface of the resilient and elastic member 90, the resilient and elastic member 90 is preferably positioned between the base portion 81 and the tip portion 82 of the pleat 80, in particular, is preferably positioned with certain distances from the base portion 81 and the tip portion 82. More specifically, the resilient and elastic member 90 is preferably positioned with a separation distance 81d of about 1 to 10 mm from the base end of the pleat 80 and with a separation distance 82d of about 1 to 10 mm from the tip of the pleat 80.

Figure 16:
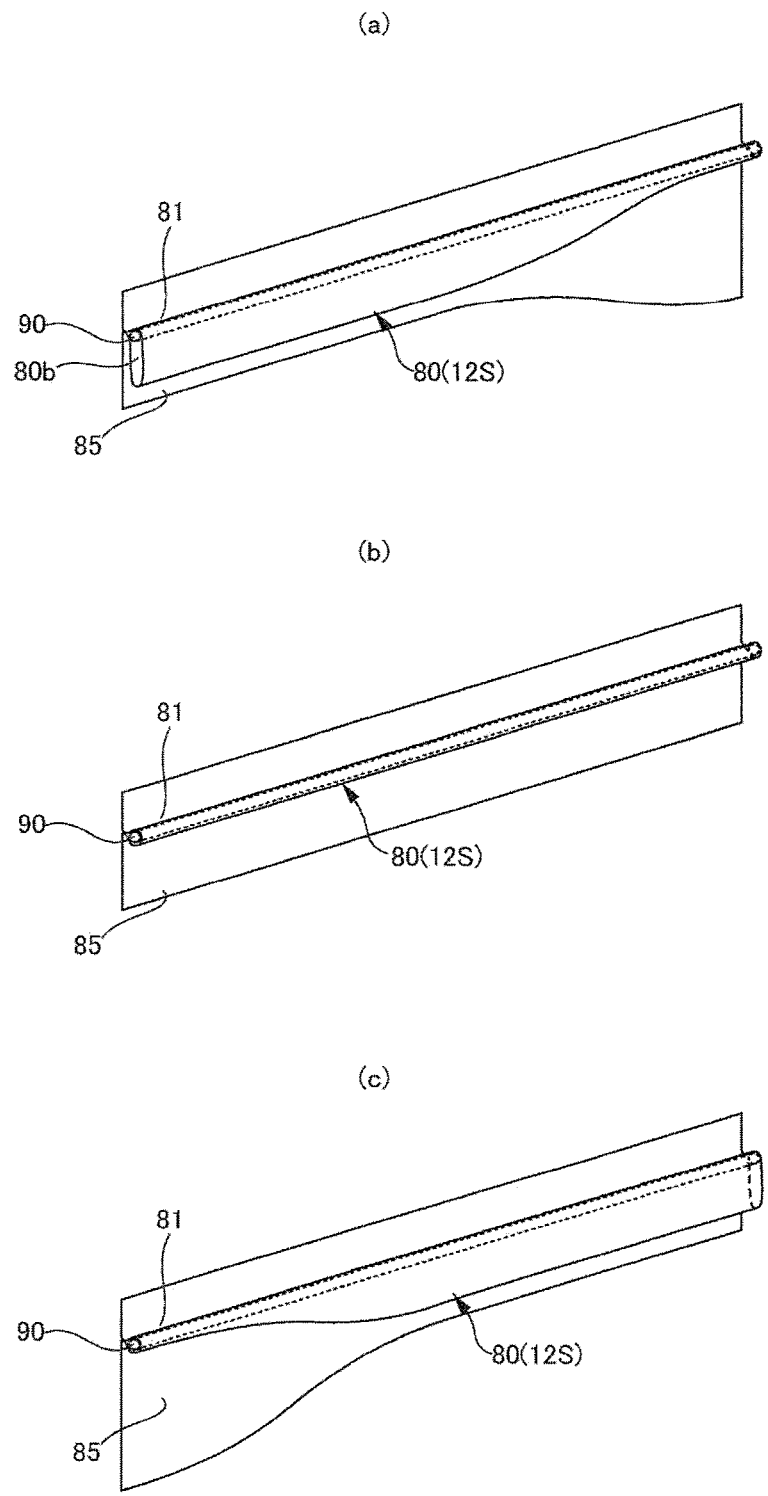
FIG. 16 is an enlarged perspective view of a main part of the outer surface of the underpants-type disposable diaper.

As illustrated in FIG. 16(b), substantially no clearance may be formed between the inner surface of the pleat 80 and the outer surface of the resilient and elastic member 90. This structure can be formed by setting the inner perimeter of the pleat 80 to be equal to or less than the outer perimeter of the resilient and elastic member 90 in the contracted state, for example. Alternatively, as in a mode described later, the clearance between the inner surface of the pleat 80 and the outer surface of the resilient and elastic member 90 may be changed in the longitudinal direction of the resilient and elastic member 90.

At the tip-side with regard to the base portions 81 of the pleats 80, the opposing surfaces 80a and 80b are preferably not joined at least at the portions except for the fixed portions of the resilient and elastic members 90. By employing at least one of the foregoing structures, the contraction wrinkles of the pleats 80 are formed in larger sizes, which increases the effect of preventing occurrence of the tightening marks described above. It is desired that one resilient and elastic member 90 is provided in one pleat 80, but two or more resilient and elastic members 90 may be provided at intervals in one pleat 80. However, in the case of providing two or more resilient and elastic members 90, all the passage positions of the resilient and elastic members 90 are also at the tip-side with regard to the base portions 81 of the pleats 80.

The resilient and elastic members 90 merely need to be fixed at least at both end portions (the end at the side seal portion 12A side and the end at the central side in the width direction in the illustrated mode) to the sheet-like member 12S. Alternatively, the resilient and elastic members 90 may be fixed intermittently in the longitudinal direction as illustrated in FIG. 9(a), or may be continuously fixed in the longitudinal direction as illustrated in FIG. 9(b). The fixing means is indicated with reference sign 83 in the drawings. The means for fixing the resilient and elastic members 90 is preferably a hot-melt adhesive. In that case, when the hot-melt adhesive is applied to the outer peripheral surfaces of the resilient and elastic members 90 and the resilient and elastic members 90 are sandwiched between the opposing surfaces 80a and 80b of the pleats 80, the opposing surfaces 80a and 80b are not joined to each other except for the fixed portions of the resilient and elastic members 90 at the tip-side with regard to the base portions 81 of the pleats 80. Taking advantage of the welding property of at least one of the resilient and elastic members 90 and the sheet-like member 12S, the resilient and elastic members 90 are sandwiched between the opposing surfaces 80a and 80b of the pleats 80 and are subjected as one body to welding process from the outsides of the pleats 80, whereby the resilient and elastic members 90 can be fixed to the sheet-like member 12S. Alternatively, the opposing surfaces 80a and 80b of the pleats 80 may be welded at the both sides of the resilient and elastic members 90 to fix the resilient and elastic members 90 by the frictional force of the resilient and elastic members 90 (refer to JP 2008-154998 A). Further, the ends of the resilient and elastic members 90 at the side seal portion 12A-sides may also be fixed by the use of the fixing force of the side seal portions 12A.

The means for fixing the resilient and elastic members 90 may vary depending on the portions of the resilient and elastic members 90. For example, the both ends of the resilient and elastic members 90 need to be firmly fixed and may be fixed by a hot-melt adhesive or welding process (including fixing by the side seal portions 12A), or both. Meanwhile, the intermediate portions of the resilient and elastic members 90 are preferably not fixed for higher flexibility. However, when the intermediate portions are merely unfixed, the positions of the resilient and elastic members 90 are not stabled. Accordingly, as illustrated in FIG. 9(c), it is desired that the opposing surfaces 80a and 80b of the pleats 80 at the both sides of the resilient and elastic members 90 are joined intermittently (or continuously) by a hot-melt adhesive or welding process in the longitudinal direction of the resilient and elastic members 90 to form joined sections 80c, and the joined sections 80c form guides for regulating the passage positions of the resilient and elastic members 90.

The pleats 80 are fixed such that the opposing surfaces 80a and 80b of at least the base portions 81 are not separated. The fixing means is shown with reference sign 84 in the drawings. When the fixing means is applied intermittently in the extending direction of the pleats 80 as illustrated in FIG. 9(a), there is an advantage in that reduction in flexibility is less prone to occur. When the fixing means is applied continuously as illustrated in FIG. 9(b), there is an advantage in that the internal welded portions of the pleats 80 and the resilient and elastic members 90 are unlikely to touch the skin. It is assumed in the illustrated modes that the opposing surfaces 80a and 80b of the base portions 81 of the pleats 80 are fixed by a hot-melt adhesive (dotted sections in the drawings). Alternatively, the opposing surfaces 80a and 80b may be fixed by welding process because the fixing by a hot-melt adhesive is inferior in adhesive power and durability to the fixing by welding, and when the opposing surfaces 80a and 80b are separated, the adhesive may touch the skin. The fixing width (length in the direction of protrusion height of the pleats) 81w of the base portions 81 can be decided as appropriate. However, when the fixed width 81w is about 1 to 5 mm, it is possible to fix reliably the base portions 81 and form the contraction wrinkles of the pleats 80 in larger sizes, thereby increasing the effects of the present invention described above.

In the case where the large number of pleats 80 are provided in the width direction in at least one of front and back regions of the diaper as in this embodiment, when the pleats 80 are fallen in the same direction at least in each of the regions having the pleats 80, uniform outer appearance and easy manufacturing are preferably achieved. The fallen direction of the pleats 80 in the front region and the fallen direction of the pleats 80 in the back region may be opposite to each other as in the illustrated mode, or may be the same (either forward or backward). However, when the wearer is to wear some clothes including trousers, spats, leggings, or tights on the underpants-type disposable diaper, it is preferable that the base portions 81 of the pleats 80 are fallen toward the waist-side and the tip portions 82 of the pleats 80 are fallen toward the crotch-side as in the illustrated mode for reducing resistance at the time of putting off the clothes. Since the pleats 80 in this embodiment extend to the side seal portions 12A, when the side seal portions 12A are fixed, the pleats 80 are also fixed in the fallen state. By arranging the pleats 80 at positions shifted in the front-back direction such that the pleats 80 at the front body part side and the pleats 80 at the back body part-side do not overlap at the side seal portions 12A, the separation strength at the side seal portions 12A less changes in the vertical direction and the side seal portions 12A are easy to tear off when the underpants-type disposable diaper is put off.

Figure 25:
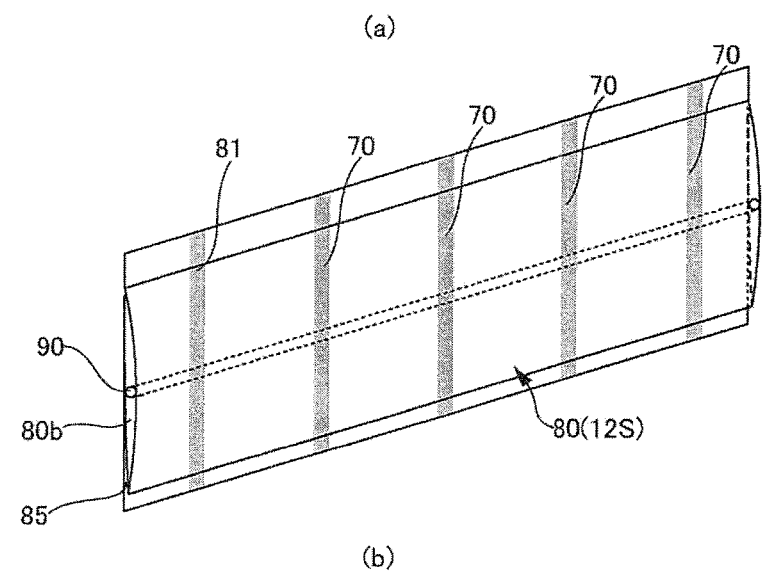
FIG. 25($a$) is a perspective view of a stretchable structure, FIG. 25($b$) is a vertical cross-sectional view of the section other than a joined section, and FIG. 25($c$) is a vertical cross-sectional view of the joined section.
Figure 25:
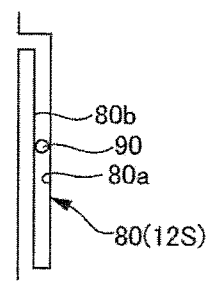
Figure 25:
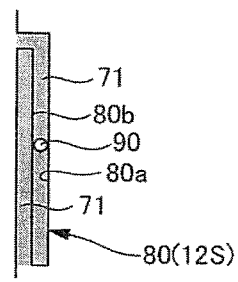

In one preferred mode, as illustrated in FIG. 25, when the opposing surfaces 80a and 80b of the pleats 80 are joined by joined sections 70 that are arranged intermittently in the stretching direction and are continuous in the direction crossing the stretching direction, and at the joined sections 70, the pleats 80 are fixed in the fallen state and the resilient and elastic member 90 are fixed between the opposing surfaces 80a and 80b of the pleats 80, contraction wrinkles extending along the stretching direction are formed intermittently in the stretching direction, thereby preferably achieving excellent air permeability and appearance. A means 71 for joining the opposing surfaces 80a and 80b of the pleats 80, fixing the pleats 80 in the fallen state, and fixing the resilient and elastic members 90 may be a hot-melt adhesive (in the mode of FIG. 25) or a welding process such as heat seal or ultrasonic seal. The joining of the opposing surfaces 80a and 80b of the pleats 80, the fixation of the pleats 80 in the fallen state, and the fixation of the resilient and elastic members 90 may be performed simultaneously by one means or separately by a plurality of means. The joining of the opposing surfaces 80a and 80b of the pleats 80 may also serve as the fixation of the opposing surfaces 80a and 80b of the base portions 81 described above.

The shape of the joined sections 70 on the opposing surfaces 80a and 80b of the pleats 80 can be decided as appropriate. In the illustrated preferable mode, the joined sections 70 are linearly continuous with a predetermined width in the direction crossing (in the illustrated mode, orthogonal to) the stretching direction. Width 70w of the joined sections 70 can be decided as appropriate, but is preferably about 1 to 4 mm (in particular, 1 to 2 mm). The interval 70d between the adjacent joined sections 70 can be decided as appropriate, but is preferably about 4 to 8 mm (in particular, 5 to 7 mm). By setting the width 70w and the interval 70d within these ranges, it is possible to provide compatibility between sufficient fluffy and prevention of irregular crushing of the pleats 80 due to compression when being packaged.

Protrusion height 80h of the pleats 80 (height of the pleats in the folded state, which is equal to the width of the inter-pleat portions 85) can be decided as appropriate but is desirably about 2 to 20 mm in general. The larger the protrusion height 80h of the pleats 80 is, the larger and thicker the wrinkles of the pleats 80 become. In addition, in the case of arranging a large number of pleats 80, the interval 80d between the pleats 80 can also be decided as appropriate but it is desirably about 2 to 30 mm in general. To prevent overlap between the adjacent pleats 80 in the fallen state, the protrusion height 80h of the pleats 80 is equal to or smaller than the interval 80d between the pleats 80. In particular, the protrusion height 80h of the pleats 80 is preferably ⅒ to ½ of the interval between the pleats 80.

Meanwhile, as illustrated in FIGS. 12 to 15, there is an underpants-type disposable diaper in which the front outer body 12F forming the ventral-side and the back outer body 12B forming the back side are not continuous but spaced from each other at the crotch-side. In the underpants-type disposable diaper, the front outer body 12F and the back outer body 12B (or at least one of them) can have the pleats 80 formed from one side seal portion 12A to the other side seal portion 12A such that the longitudinal direction of the pleats 80 aligns with the width direction, and a stretchable structure with the pleats 80 can be provided in the region at least including the both sides sandwitching the inner body 200 in the width direction. In this case, the stretchable structure may have the uniform protrusion height of the pleats 80 or may be configured such that the protrusion height of the pleats 80 progressively decreases from the side seal portions 12A at the both sides toward the center in the width direction and, according to this, the edges at the crotch-side swell toward the crotch-side as in the illustrated mode. For example, the protrusion height of the pleats 80 is progressively decreased from the left side toward the center in the width direction and the edges at the crotch-side are extended by the decreased height toward the crotch-side as illustrated in FIG. 16(a), and the protrusion height of the pleats 80 is the smallest at the central portion in the width direction (for example, the region of the inner body 200 joined to the outer body 12) as illustrated in FIG. 16(b), and the protrusion height of the pleats 80 is progressively increased from the intermediate portion toward the right side and toward the left side in the width direction symmetrically as illustrated in FIG. 16(b). By progressively decreasing the protrusion height of the pleats 80 from the side seal portions 12A at the both sides toward the center in the width direction as described above, the front-back length necessary for the formation of the pleats 80 becomes short at the central side in the width direction, and by extending the excess portion toward the crotch-side, the edges of the outer body 12 at the crotch-side can be swollen toward the crotch-side. As a result, out of the edges of the outer body 12 at the crotch-side, the edges around the legs extended to the both sides of the inner body 200 in the width direction can be formed along the peripheries of the groin region and the buttocks. In addition, since the protrusion height of the pleats 80 overlapping the inner body 200 is decreased, the post-treatment tape 70 is unlikely to be mistakenly unfastened or fallen by arranging the post-treatment tape 70 at a position with the smaller protrusion height of the pleats 80, as in the illustrated mode.

Further, in this mode, by forming slits 86 in the inter-pleat portions 85 (in particular, at one or more spots at the crotch-side) along the longitudinal direction of the pleats 80 and extending the slits 86 toward the crotch-side, the edges of the outer body 12 at the crotch-side can be further swollen toward the crotch-side. When the length of the slits 86 is larger than the width of the region of the inner body 200 joined to the outer body 12, the slits are opened to the outer body 12. Accordingly, the length of the slits 86 is preferably equal to or less than the width of the joined region of the inner body 200, and in particular, is smaller than the width of the joined region of the inner body 200. In the case of providing the slits 86, a cutting pattern for the slits 86 is preferably integrated with a cutting pattern for finely cutting the resilient and elastic members 15 and 16 at the central portion in the width direction overlapping the inner body 200, thereby to perform simultaneously and integrally cutting processes for the slits 86 and the resilient and elastic members 15 and 16.

Figure 26:
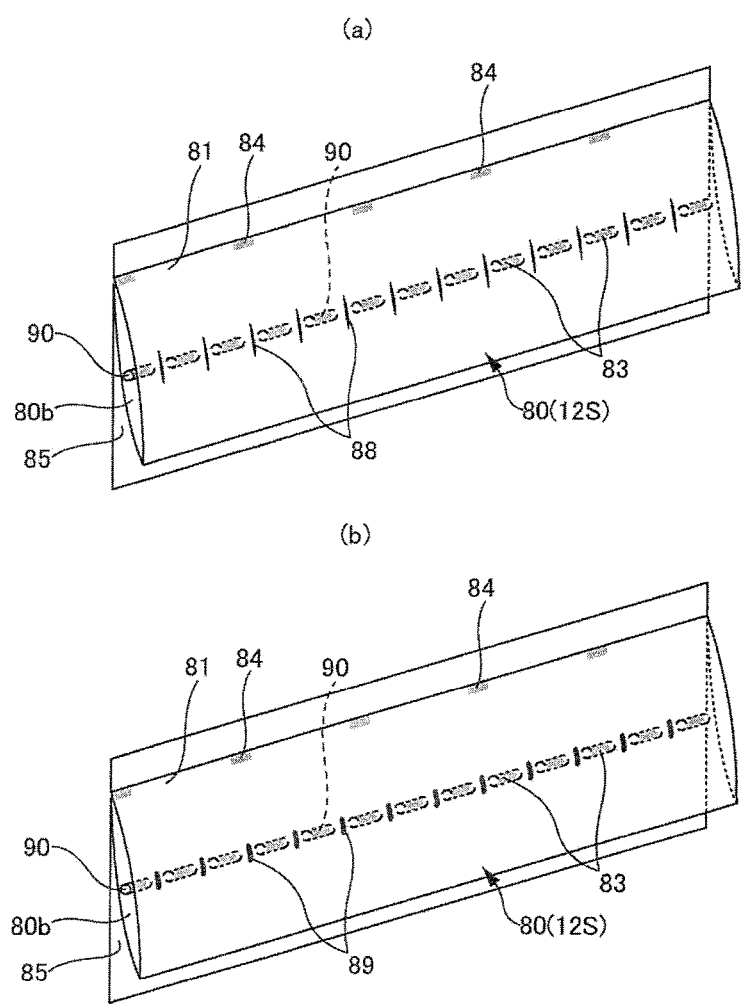
FIG. 26 represents perspective views of a stretchable structure.

On the other hand, in the case of finely cutting the resilient and elastic members 90 in the partial or entire region overlapping the inner body 200 in the underpants-type disposable diaper to eliminate stretching properties as described above, when the resilient and elastic members 90 are cut together with the air permeable material 120 from the outside of the pleats 80 as illustrated in FIG. 26(*a*), cut lines 88 are formed in the pleats 80. Accordingly, the pleats 80 are prone to be open due to the formation of the cut lines 88, thereby causing deterioration in outer appearance and texture. It is thus desired that the resilient and elastic members 90 in the pleats 80 are finely cut but the air permeable material 120 forming the pleats 80 is not cut as illustrated in FIG. 26(*b*). The cutting of the resilient and elastic members 90 can be performed by subjecting the resilient and elastic members 90 together with the air permeable material 120 to pressurizing and heating processes through heat seal or ultrasonic seal from the outside of the pleats 80. In this case, welding marks 89 of the air permeable material 120 are left on the outer surface of the pleats 80 at the cut positions of the resilient and elastic members 90, but no cut lines or holes are opened and only the resilient and elastic members 90 inside are cut. The opposing surfaces 80*a* and 80*b* of the pleats 80 may or may not be joined by the pressurizing and heating processes.

(Others)

In the foregoing example, the stretchable structure is applied to the area from the waist lower portions U to the intermediate portion L of the underpants-type disposable diaper. Besides, the stretchable structure may also be applied to the waist edge portions W. The resilient and elastic members 16 may not be provided in the intermediate portion L. In addition, the foregoing elastic structure can also be applied to the waist portion of the back side of the tape-type disposable diaper described above in relation to the related art, the three-dimensional gathers, and other stretchable portions.

In the foregoing example, the pleats 80 protrude toward the side opposite to the skin-contact-side, and the inter-pleat portions 85 overlap the skin-sides of the pleats 80 in the fallen state. Alternatively, the pleats 80 may protrude toward the skin-side.

(Method for Forming the Stretchable Structure)

Figure 17:
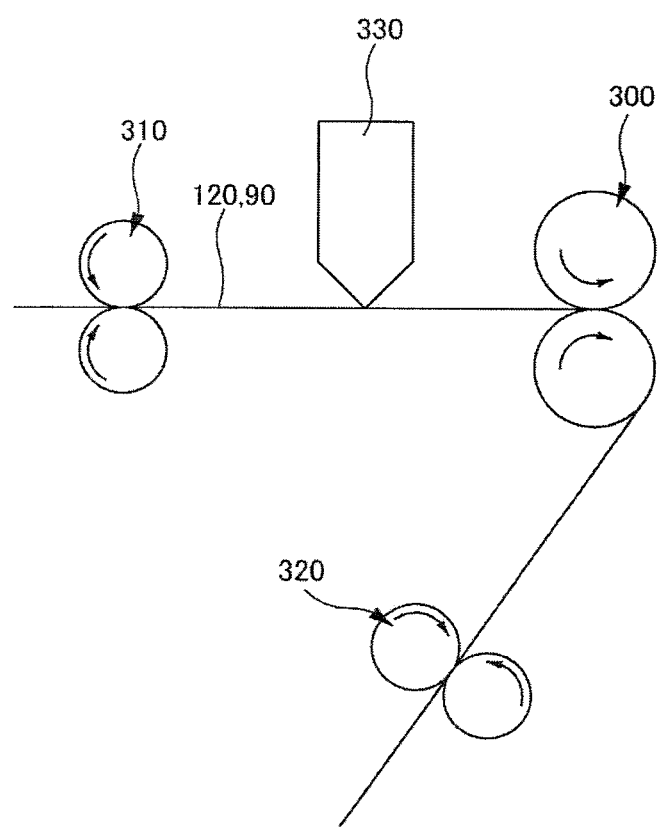
FIG. 17 is a schematic view of a manufacturing line.
Figure 18:
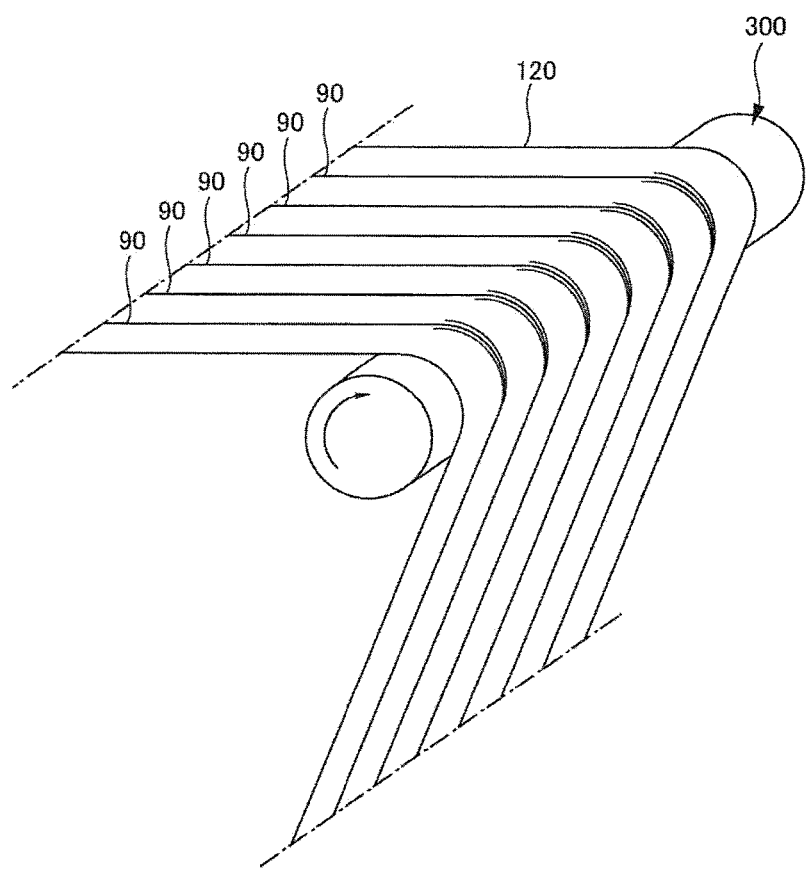
FIG. 18 is a perspective view illustrating schematically the manufacturing line.
Figure 19:
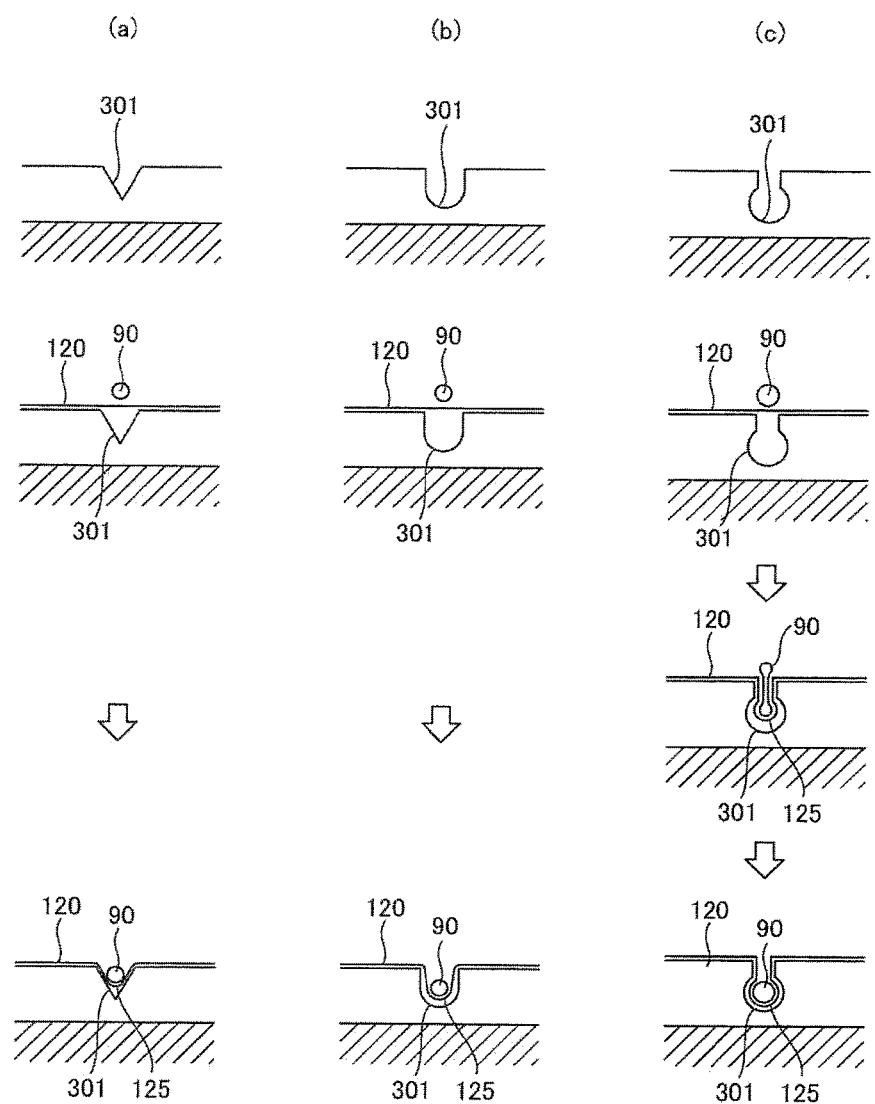
FIG. 19 represents schematic views of pleat formation rolls.

There is no particular limitation on the method for manufacturing the stretchable structure in which the sheet-like member 12S is formed from one air permeable material. For example, a technique by which one air permeable material is folded and fixed by a sailor and resilient and elastic members are sandwiched in the air permeable material (method for use in the manufacture of the three dimensional gathers 60) may be applied. In addition, the method shown in FIGS. 17 and 18 is proposed. Specifically, according to the method for forming the stretchable structure for absorbent article, a pleat formation roll 300 with circumferentially continuous grooves 301 in an outer peripheral surface is rotary driven around a shaft center, a continuous belt-like air permeable material 120 is wound around the outer peripheral surface and passed in a rotating direction, elongated resilient and elastic members 90 are supplied in a line flow direction to the groove passage position of the air permeable material 120 at an entry side of the pleat formation roll 300, a line tension of the air permeable material 120 at the entry side of the pleat formation roll 300 is set as a line tension to generate a width reduction of the air permeable material 120, a line tension of the air permeable material at an exit side of the pleat formation roll 300 is set as a line tension to return from the width reduction, the portion of the air permeable material 120 returned from the width reduction is pushed into the grooves 301 under a line tension of the resilient and elastic members 90 by decrease in the line tension on the pleat formation roll 300 to form pleat-like portions 125 in the air permeable material 120 as illustrated in FIGS. 18 and 19, opposing surfaces of the pleat-like portions 125 are joined such that they are not separated at least at base portions of the pleat-like portions 125, and, after the supply of the resilient and elastic members 90, at least both end portions of the resilient and elastic members 90 are fixed between the opposing surfaces of the pleat-like portions 125.

To create changes in the line tension at the entry side and the exit side of the pleat formation roll 300, in the illustrated mode, an entry side carrying roll 310 and an exist side carrying roll 320 are provided at the entry side and the exist side of the pleat formation roll 300, the air permeable material 120 is wound around the entry side carrying roll 310, the pleat formation roll 300, and the exist side carrying roll 320 in sequence, the pleat formation roll 300 is driven at a higher rotational speed than the rotational speed of the entry side carrying roll 310, and the exist side carrying roll 320 is driven at a lower rotational speed than the rotational speed of the pleat formation roll 300. Making the changes in the line speeds can produce the changes in the line tension (tension applied to the air permeable material 120 in the carrying direction at the time of carrying) as described above. By decreasing the line tension on the pleat formation roll 300, the portion of the air permeable material 120 returned from the width reduction can be pushed into the grooves 301 under the line tension of the resilient and elastic members 90 to form the pleat-like portions 125 in the air permeable material 120 as illustrated in FIGS. 18 and 19.

There is no particular limitation on the means for fixing the pleat-like portions 125 in the air permeable material 120. In the illustrated mode, an application device 330 arranged on the upstream side of the pleat formation roll 300 applies a hot-melt adhesive continuously or intermittently to the base portions 81 of the pleats 80 in the air permeable material 120, and the air permeable material 120 is pushed into the grooves 301 in the pleat formation roll 300, whereby the base portions 81 are opposed and adhered to each other. Alternatively, the exit side carrying roll 320 may be made as a roll with grooves 301 similar to those in the pleat formation roll 300 such that the air permeable material 120 holding the resilient and elastic members 90 in the pleat-like portions 125 are carried from the pleat formation roll 300 to the exit side carrying roll 320, and the base portions 81 of the pleats 80 are sandwiched and welded from both sides between welding rolls such as heating rolls.

Figure 21:
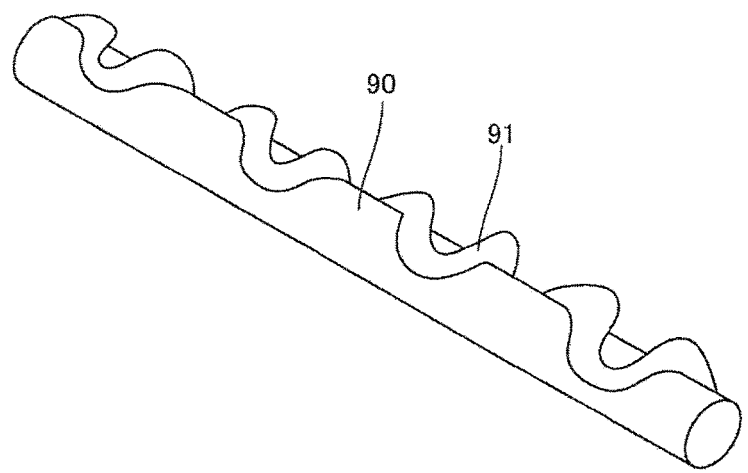
FIG. 21 is a perspective view schematically illustrating a mode of application of a hot-melt adhesive.

The resilient and elastic members 90 may be fixed continuously or intermittently in the longitudinal direction or may be fixed only at the both ends. The means for fixing the resilient and elastic members 90 may be a hot-melt adhesive or welding. In the case of fixing the resilient and elastic members 90 by a hot-melt adhesive, the resilient and elastic members 90 with the hot-melt adhesive applied to the outer peripheral surface may be stuck to the air permeable material 120, or the hot-melt adhesive may be applied in advance to the air permeable material 120 and then the resilient and elastic members 90 be stuck to the air permeable material 120. For the application of the hot-melt adhesive to the outer peripheral surfaces of the resilient and elastic members 90, a hot-melt adhesive 91 may be applied by Surewrap Nozzle as illustrated in FIG. 21 or by a comb-gun. In the mode illustrated in FIG. 17, it is assumed that the resilient and elastic members 90 with the hot-melt adhesive applied to the outer peripheral surfaces are stuck to the air permeable material 120 on the upstream side of the entry side carrying roll 310. The resilient and elastic members 90 may be fixed at any timing after the supply of the resilient and elastic members 90, such as during the passage from the entry side carrying roll 310 to the pleat formation roll 300, or after the passage through the pleat formation roll 300 when the fixing means is welding.

The shape of the grooves 301 in the pleat formation roll 300 can be decided as appropriate. The grooves 301 may be V-shaped grooves 301 with a V-shaped cross section as illustrated in FIG. 19(a), U-shaped grooves 301 with a U-shaped cross section as illustrated in FIG. 19(b), or narrow-entry grooves 301 with an inverse Ω-shaped cross section having a narrow entry and a wide bottom as illustrated in FIG. 19(c). In particular, in the former two modes, the base portions 81 of the pleats 80 can be joined by an adhesive but the intervals between the opposing surfaces 80a and 80b of the base portions 81 are likely to be wide. Meanwhile, in the narrow-entry grooves 301 illustrated in FIG. 19(c), the interval between the opposing surfaces 80a and 80b of the base portions 81 is narrow to allow more reliable adhesion. When the entry width of the narrow-entry grooves 301 is equal to or more than the dimension obtaining by adding the twofold thickness of the air permeable material 120 to the diameter of the resilient and elastic members 90 in the line and is equal to or less than the dimension obtained by adding the twofold thickness of the air permeable material 120 to the diameter of the resilient and elastic members 90 with a natural length, the resilient and elastic members 90 and the air permeable material 120 can be smoothly pushed into the grooves 301. Even when the entry width of the narrow-entry grooves 301 is set to be equal to or less than the dimension obtained by adding the twofold thickness of the air permeable material 120 to the diameter of the resilient and elastic members 90 in the manufacture line as illustrated in FIG. 19(c), the resilient and elastic members 90 and the air permeable material 120 can be pushed into the grooves 301 due to the deformation of the resilient and elastic members 90. In particular, by applying a hot-melt adhesive to the outer peripheral surfaces of the resilient and elastic members 90, the hot-melt adhesive is spread to the opposing surfaces 80a and 80b of the base portions 81 of the pleats 80 due to the deformation of the resilient and elastic members 90 to contribute to the adhesion of the base portions 81 of the pleats 80 as well.

Figure 20:
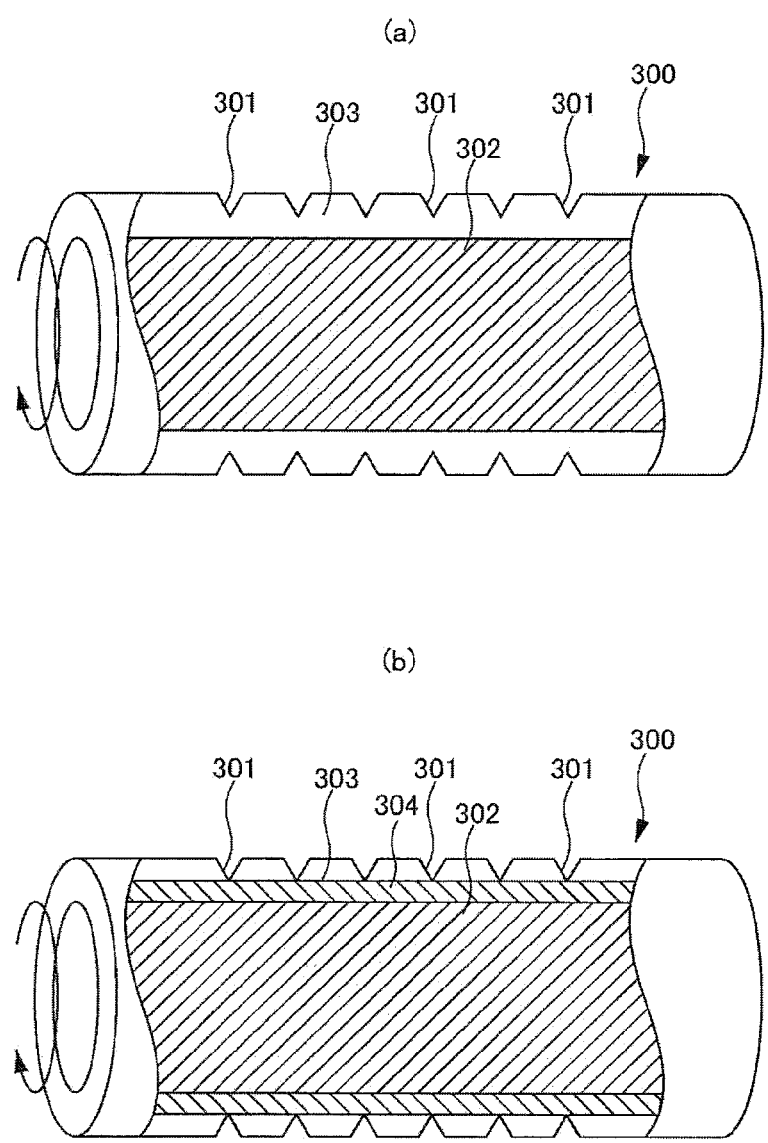
FIG. 20 represents perspective views illustrating schematically a process of forming pleats and a process of fixing resilient and elastic members.

The pleat formation roll 300 may be a roll with the outer peripheral surface made of metal. However, the pleat formation roll 300 is preferably a rubber roll formed by providing a rubber layer 303 having grooves 301 on the outer periphery of a shaft portion 302 as illustrated in FIG. 20(a). Nevertheless, taking into consideration the problem of abrasion of the bottom of the grooves, the bottom of the grooves may be favorably made of a metal layer 304 as illustrated in FIG. 20(b).

Figure 22:
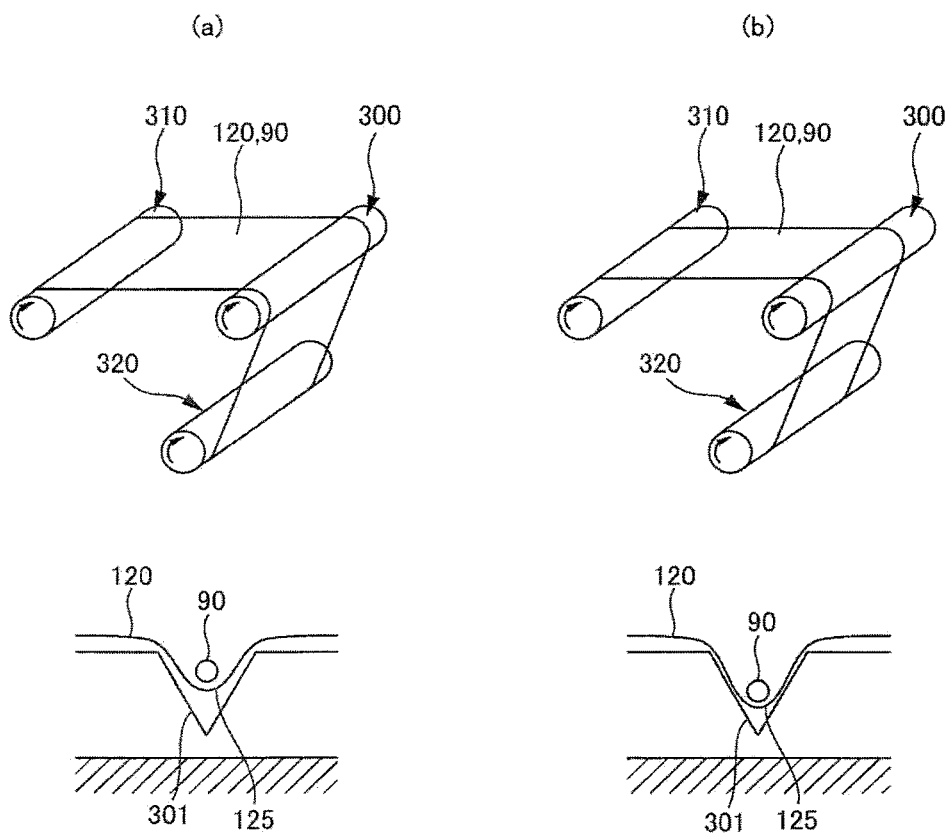
FIG. 22 represents explanatory diagrams illustrating a relationship between width reduction and protrusion height of a pleat.

Meanwhile, when the line tension state with small width reduction and return from the reduction as illustrated in the upper part of FIG. 22(a) and the line tension state with large width reduction and return from the reduction as illustrated in the upper part of FIG. 22(b) are alternately repeated at predetermined timing, the protrusion height of the pleat-like portions 125 becomes small in the line tension state with small width reduction and return from the reduction as illustrated in the lower part of FIG. 22(a), and the protrusion height of the pleat-like portions 125 becomes large in the line tension state with large width reduction and return from the reduction as illustrated in the lower part of FIG. 22(b). Therefore, according to this method, it is possible to form the stretchable structure in the mode illustrated in FIGS. 12 to 16 described above.

The line tension state with small width reduction and return from the reduction as illustrated in FIG. 22(a) can be produced by driving and controlling the rolls 300, 310, and 320 to decrease the difference in rotational speed between the entry side carrying roll 310 and the pleat formation roll 300 and decrease the difference in rotational speed between the pleat formation roll 300 and the exist side carrying roll 320, shorten the spacing between the entry side carrying roll 310 and the pleat formation roll 300 in the carrying direction, and shorten the spacing between the pleat formation roll 300 and the exist-side carrying roll 320 in the carrying direction, for example. In addition, the line tension state with large width reduction and return from the reduction as illustrated in FIG. 22(b) can be produced by driving and controlling the rolls 300, 310, and 320 to increase the difference in rotational speed between the entry side carrying roll 310 and the pleat formation roll 300, increase the difference in rotational speed between the pleat formation roll 300 and the exist side carrying roll 320, lengthen the spacing between the entry side carrying roll 310 and the pleat formation roll 300 in the carrying direction, and lengthen the spacing between the pleat formation roll 300 and the exist side carrying roll 320 in the carrying direction, for example.

Figure 23:
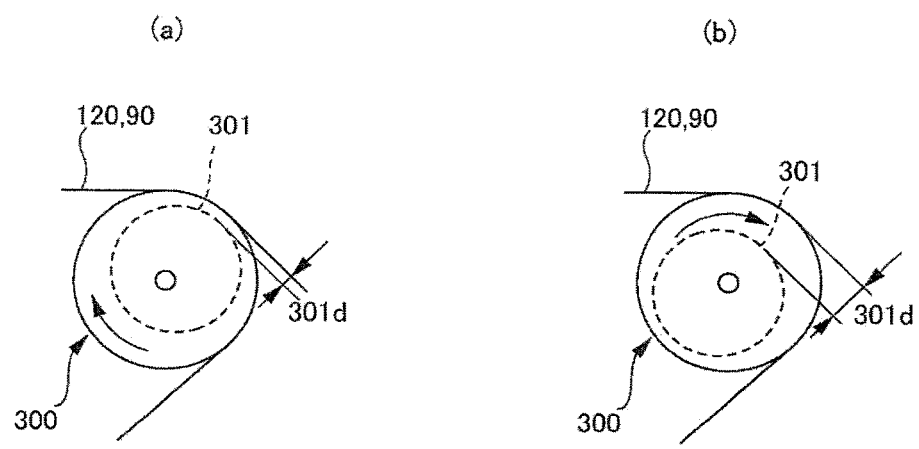
FIG. 23 represents schematic views of changes in depth of a groove in the pleat formation roll.

Further, by using a roll with circumferential changes in depth 301d of the grooves 301 as illustrated in FIG. 23 (FIG. 23(a) shows the state in which the depth 301d is shallow and FIG. 23(b) shows the state in which the depth 301d is deep) as the pleat formation roll 300 and changing the protrusion height of the pleat-like portions 125 in the line flow direction, it is possible to form the stretchable structure in the mode illustrated in FIGS. 12 to 16.

Figure 24:
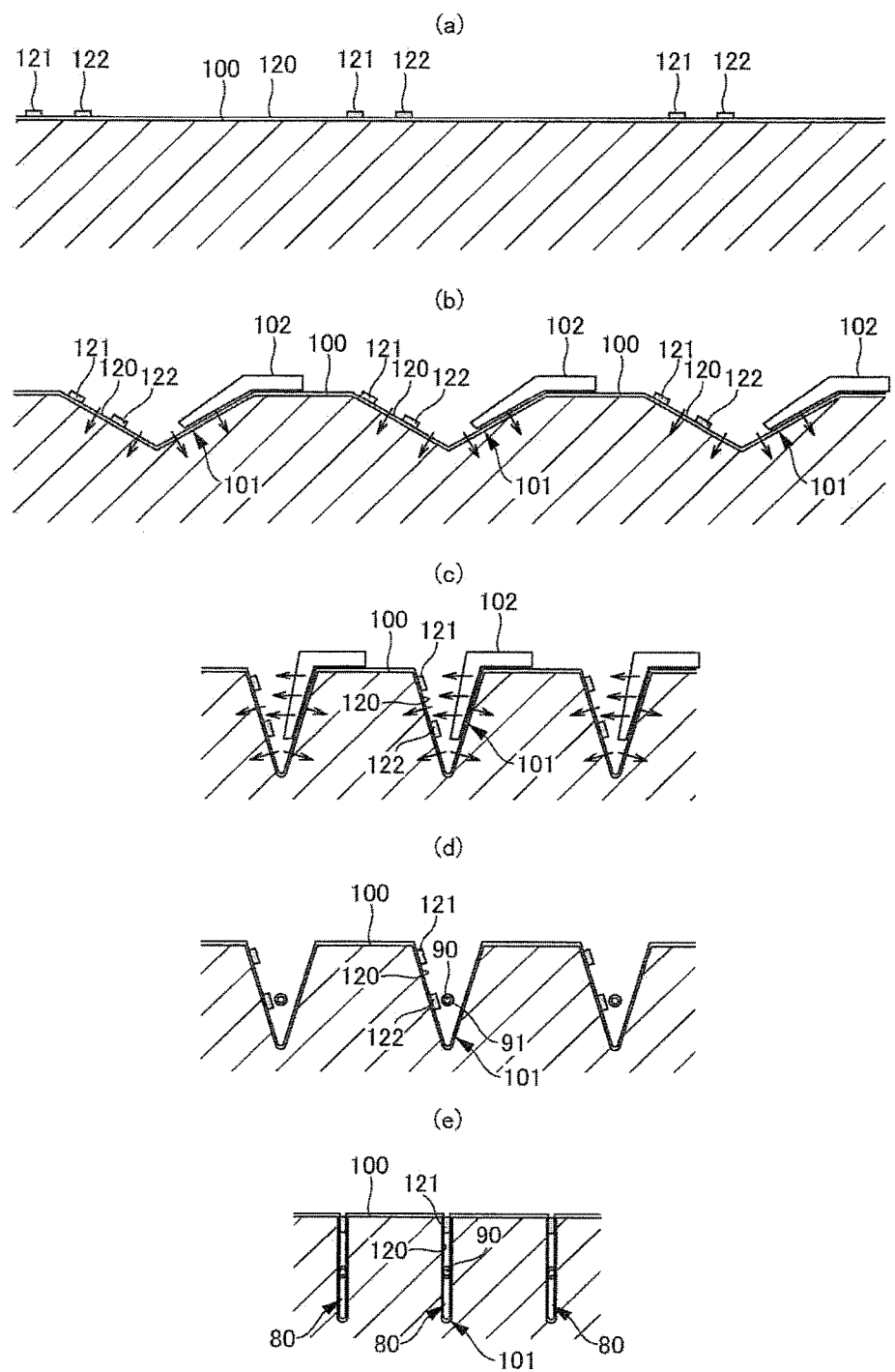
FIG. 24 represents schematic views illustrating manufacturing principles.

As another method for forming the stretchable structure, a technique shown in FIG. 24 may be used, for example. Specifically, according to this method for forming the stretchable structure, while one air permeable material 120 is first carried in a flat state over a flat carrying surface 100 in a manufacture line as illustrated in FIG. 24(a), a base portion adhesive 121 is applied to the air permeable material 120 to adhere the opposing surfaces 80a and 80b of the base portions 81 of the pleats 80. In order to form a large number of pleats 80 as in the mode described above, the base portion adhesive 121 is applied in correspondence with the number of the pleats 80. In addition, an intermediate portion adhesive 122 is preferably applied to the fixed positions of the resilient and elastic members 90. The intermediate portion adhesive 122 may be applied to either of the opposing surfaces 80a and 80b of the pleats 80 as in the illustrated mode, or may be applied to the both surfaces. The application of the intermediate portion adhesive 122 may be performed concurrently with the application of the base portion adhesive 121, or before or after the same.

Next, as illustrated in FIGS. 24(b) and 24(c), while the air permeable material 120 is carried over the carrying surface 100 with V-shaped grooves 101 extending in the carrying direction (orthogonal to the illustrated plane) and formed at intervals in the CD direction (lateral direction orthogonal to the carrying direction), the air permeable material 120 is sucked from the inner surfaces of the V-shaped grooves 101 as indicated by arrows. FIG. 24(c) illustrates the state on the downstream side of the state illustrated in FIG. 24(b). As understood from this positional relationship in the drawings, the V-shaped grooves 101 are formed such that the central spacing in the V-shaped grooves 101 becomes continuously narrower with increasing proximity toward the downstream side in the carrying direction, and the inclination angle of the both side surfaces of the V-shaped grooves 101 becomes continuously larger with increasing proximity toward the downstream side in the carrying direction. Therefore, the air permeable material 120 on the carrying surface 100 is deformed by the suction along the V-shaped grooves, and the portions of the air permeable material 120 positioned in the V-shaped grooves 101 are folded with increase in the inclination angle of the both side surfaces of the V-shaped grooves 101.

To fold smoothly the air permeable material 120 in the V-shaped grooves 101, it is more preferred that press plates 102 are arranged at least at one each shoulder portion of the V-shaped grooves 101 as illustrated in FIGS. 24(b) and 24(c) (the press plates 102 are arranged at only one each shoulder portion in the illustrated example, but may be arranged at the both shoulder portions). In addition, air may be blown to at least one each side surface of the V-shaped grooves 101 from the press plates 102 as indicated by arrows in FIG. 24(c) (air is blown to only one each side surface in the illustrated example, but may be blown to the both side surfaces).

Next, as illustrated in FIG. 24(d), the resilient and elastic members 90 are introduced along the carrying direction into between opposing inner surfaces of the V-shaped air permeable material 120 folded to some extent, and are held at the position. In the case of not applying the intermediate portion adhesive 122 or in order to maintain more strong adhesive force, a hot-melt adhesive 91 may be applied in advance by Surewrap Nozzle, a comb gun, or the like to the outer peripheral surface of the resilient and elastic members 90 as in the illustrated mode.

After that, as illustrated in FIG. 24(e), when the inclination angle of the both side surfaces of the V-shaped grooves 101 in the carrying surface 100 further increases, the portions of the air permeable material 120 positioned in the V-shaped grooves 101 are completely folded. The opposing side surfaces of the air permeable material 120 are adhered to each other and the resilient and elastic members 90 are fixed to the air permeable material 120 by the base portion 81 adhesive and, if any, the intermediate portion adhesive 122 and an adhesive applied to the outer peripheral surfaces of the resilient and elastic members 90. Accordingly, the stretchable structure with the large number of pleats 80 can be formed in a continuous and concurrent manner.

<Descriptions of the Terms Used Herein>

Unless otherwise specified herein, the terms used herein have the meanings described below.

The water absorption capacity is measured by carrying out JIS K7223-1996 "Testing method for water absorption capacity of super absorbent polymers."

The water absorption rate is determined as "time that elapses before the end point" by carrying out JIS K7224-1996 "Testing method for water absorption rate of super absorbent polymers" using 2 g of high absorbent polymer and 50 g of saline.

The "extension ratio" refers to a value with respect to 100% representing the natural length.

The "gel strength" is measured in such a manner as described below. That is, a high-absorbent polymer of 1.0 g is added to an artificial urine of 49.0 g (urea: 20 wt %, salt: 8 wt %, calcium chloride dihydrate 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

The "basis weight" is measured in such a manner as described below. That is, a specimen or a test piece is preliminarily dried and left stand in a test room or a test device in a standard state (at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$).

INDUSTRIAL APPLICABILITY

The present invention is suited to underpants-type disposable diapers as described above but is also applicable to tape-type or pad-type disposable diapers and other general absorbent articles such as sanitary napkins.

REFERENCE SIGNS LIST

11 Liquid impervious sheet
12 Outer body
12A Side seal portion
12B Back outer body
12F Front outer body
12M Crotch portion outer body
12S Sheet-like member
12r Folded portion
25 Printed sheet
30 Top sheet
40 Intermediate sheet
50 Absorbent element
56 Absorber
58 Wrapping sheet
60 Three-dimensional gather
62 Gather sheet
70 Post-treatment tape
80 Pleat
80a and 80b Opposing surface
81 Base portion
82 Tip portion
85 Inter-pleat portion
86 Slit
90 Resilient and elastic member
100 Carrying surface
101 V-shaped groove
102 Press plate
120 Air permeable material
121 Base portion adhesive
122 Intermediate portion adhesive
125 Pleat-like portion
200 Inner body
300 Pleat formation roll
301 Groove
310 Entry side carrying roll
320 Exit side carrying roll
330 Application device

The invention claimed is:

1. A stretchable structure for absorbent article, comprising:
   a sheet-like member that is composed of one air permeable material and has a plurality of pleats arranged at intervals so as not to overlap in a fallen state and inter-pleat portions overlapping in the state in which the pleats are fallen; and
   elongated resilient and elastic members provided between opposing surfaces of the pleats along a longitudinal direction of the pleats, wherein
   the opposing surfaces of the pleats are continuously or intermittently joined in the longitudinal direction of the pleats such that the opposing surfaces of each pleat are not separated at least at a base portion of the pleat,
   outer surfaces of the pleat are not joined to the inter-pleat portions except for at both longitudinal ends of the pleats,
   resilient and elastic members are arranged in the pleats at a tip-side with regard to the base portion and at least both ends of the resilient and elastic members are fixed between the opposing surfaces of the pleats,
   the pleats and the inter-pleat portions are contracted by contraction of the resilient and elastic members,
   the pleat protrude to a side opposite to a skin-contact-side, and
   inter-pleat portions overlap the skin-side of the pleats in the fallen state.

2. The stretchable structure for absorbent article according to claim 1, wherein the large number of pleats are provided along the width direction in at least one of front and back areas of the absorbent article, and are fallen in the same direction in at least each area having the pleats.

3. The stretchable structure for absorbent article according to claim 1, wherein protrusion height of pleats is $\frac{1}{10}$ to $\frac{1}{2}$ of the interval between the pleats.

4. The stretchable structure for absorbent article according to claim 1, wherein
   resilient and elastic members are arranged to pass between the base portions and tip portions of pleats and pass through a position spaced apart from the base portions and apart from the tip portions, and
   the opposing surfaces of the pleats, except for at the fixed portions of the resilient and elastic members, are not joined at the tip-side with regard to the base portion.

5. The stretchable structure for absorbent article according to claim 1, wherein the protrusion height of the pleats is larger than the interval between the pleats.

6. A stretchable structure for absorbent article, comprising:
   a sheet-like member that is composed of one air permeable material and has a plurality of pleats arranged at intervals so as not to overlap in a fallen state and inter-pleat portions overlapping in the state in which the pleats are fallen; and
   elongated resilient and elastic members provided between opposing surfaces of the pleats along a longitudinal direction of the pleats, wherein
   the opposing surfaces of the pleats are continuously or intermittently joined in the longitudinal direction of the pleats such that the opposing surfaces of each pleat are not separated at least at a base portion of the pleat,
   outer surfaces of the pleat are not joined to the inter-pleat portions except for at both longitudinal ends of the pleats,
   resilient and elastic members are arranged in the pleats at a tip-side with regard to the base portion and at least both ends of the resilient and elastic members are fixed between the opposing surfaces of the pleats,
   the pleats and the inter-pleat portions are contracted by contraction of the resilient and elastic members, and
   the opposing surfaces of the pleats are joined by joined sections that are intermittently arranged in the stretching direction and continuous in the direction crossing the stretching direction, and, at the joined sections, the pleats are fixed in the fallen state and the resilient and elastic members are fixed between the opposing surfaces of the pleats.

7. An absorbent article comprising:
   an stretchable structure for absorbent article, comprising:
      a sheet-like member that is composed of one air permeable material and has a plurality of pleats arranged at intervals so as not to overlap in a fallen state and inter-pleat portions overlapping in the state in which the pleats are fallen; and
      elongated resilient and elastic members provided between opposing surfaces of the pleats along a longitudinal direction of the pleats, wherein
      the opposing surfaces of the pleats are continuously or intermittently joined in the longitudinal direction of the pleats such that the opposing surfaces of each pleat are not separated at least at a base portion of the pleat,
      outer surfaces of the pleat are not joined to the inter-pleat portions except for at both longitudinal ends of the pleats,
      resilient and elastic members are arranged in the pleats at a tip-side with regard to the base portion and at least both ends of the resilient and elastic members are fixed between the opposing surfaces of the pleats, and
      the pleats and the inter-pleat portions are contracted by contraction of the resilient and elastic members, wherein
   the absorbent article is an underpants-type disposable diaper, including: an outer body constituting individually or integrally a front body part and a back body part; and an inner body including an absorber and fixed to an inner surface of the outer body, the front body part of the outer body and the back body part of the outer body being joined at both sides to form side seal portions, thereby forming an annular waist portion and a waist opening and a pair of right and left leg openings,
   the stretchable structure is provided in an area of the outer body including at least both sides sandwiching the inner body in the width direction such that the longitudinal direction of the pleats is aligned with the width direction,
   the outer body is composed of a front outer body constituting the front body part and a back outer body constituting the back body part, the front outer body and the back outer body being not continuous but spaced from each other at a crotch-side, and
   at least one of the front outer body and the back outer body has the pleats formed from one side seal portion to the other side seal portion such that the longitudinal direction of the pleats is aligned with the width direction, and the stretchable structure is formed by the pleats in an area including at least the both sides sandwiching the inner body in the width direction, the protrusion height of the pleats becomes progressively smaller from the side seal portions at the both sides toward the center in the width direction, and edges at the crotch-side swell toward the crotch-side.

8. An absorbent article comprising:
an stretchable structure for absorbent article, comprising:
- a sheet-like member that is composed of one air permeable material and has a plurality of pleats arranged at intervals so as not to overlap in a fallen state and inter-pleat portions overlapping in the state in which the pleats are fallen; and
- elongated resilient and elastic members provided between opposing surfaces of the pleats along a longitudinal direction of the pleats, wherein
- the opposing surfaces of the pleats are continuously or intermittently joined in the longitudinal direction of the pleats such that the opposing surfaces of each pleat are not separated at least at a base portion of the pleat,
- outer surfaces of the pleat are not joined to the inter-pleat portions except for at both longitudinal ends of the pleats,
- resilient and elastic members are arranged in the pleats at a tip-side with regard to the base portion and at least both ends of the resilient and elastic members are fixed between the opposing surfaces of the pleats, and
- the pleats and the inter-pleat portions are contracted by contraction of the resilient and elastic members, wherein the absorbent article is an underpants-type disposable diaper, including: an outer body constituting individually or integrally a front body part and a back body part; and an inner body including an absorber and fixed to an inner surface of the outer body, the front body part of the outer body and the back body part of the outer body being joined at both sides to form side seal portions, thereby forming an annular waist portion and a waist opening and a pair of right and left leg openings, the stretchable structure is provided in an area of the outer body including at least both sides sandwiching the inner body in the width direction such that the longitudinal direction of the pleats is aligned with the width direction, the outer body is composed of a front outer body constituting the front body part and a back outer body constituting the back body part, the front outer body and the back outer body being not continuous but spaced from each other at a crotch-side, and at least one of the front outer body and the back outer body has the pleats formed from one side seal portion to the other side seal portion such that the longitudinal direction of the pleats is aligned with the width direction, and has slits between the pleats in a central portion in the width direction along the longitudinal direction of the pleats, the slits being increased in width at the crotch-side to swell the edges of the crotch-side toward the crotch-side.

9. An absorbent article comprising:
an stretchable structure for absorbent article, comprising:
- a sheet-like member that is composed of one air permeable material and has a plurality of pleats arranged at intervals so as not to overlap in a fallen state and inter-pleat portions overlapping in the state in which the pleats are fallen; and
- elongated resilient and elastic members provided between opposing surfaces of the pleats along a longitudinal direction of the pleats, wherein
- the opposing surfaces of the pleats are continuously or intermittently joined in the longitudinal direction of the pleats such that the opposing surfaces of each pleat are not separated at least at a base portion of the pleat,
- outer surfaces of the pleat are not joined to the inter-pleat portions except for at both longitudinal ends of the pleats,
- resilient and elastic members are arranged in the pleats at a tip-side with regard to the base portion and at least both ends of the resilient and elastic members are fixed between the opposing surfaces of the pleats, and
- the pleats and the inter-pleat portions are contracted by contraction of the resilient and elastic members, wherein the absorbent article is an underpants-type disposable diaper, including: an outer body constituting individually or integrally a front body part and a back body part; and an inner body including an absorber and fixed to an inner surface of the outer body, the front body part of the outer body and the back body part of the outer body being joined at both sides to form side seal portions, thereby forming an annular waist portion and a waist opening and a pair of right and left leg openings, the stretchable structure is provided in an area of the outer body including at least both sides sandwiching the inner body in the width direction such that the longitudinal direction of the pleats is aligned with the width direction, and the pleats are formed at both the front body part of the outer body and the back body part of the outer body from the one side seal portion to the other side seal portion such that the longitudinal direction of the pleats align with the width direction, and the pleats in the front body part and the pleats in the back body part are shifted in position in the front-back direction such that the pleats in the front body part and the pleats in the back body part do not overlap at the side seal portions.

* * * * *